United States Patent
Shoshan-Barmatz

(10) Patent No.: US 11,408,887 B2
(45) Date of Patent: Aug. 9, 2022

(54) BIOMARKERS FOR DIAGNOSIS OF LUNG CANCER

(71) Applicant: THE NATIONAL INSTITUTE FOR BIOTECHNOLOGY IN THE NEGEV LTD., Beer Sheva (IL)

(72) Inventor: Varda Shoshan-Barmatz, Omer (IL)

(73) Assignee: THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 159 days.

(21) Appl. No.: 16/615,147

(22) PCT Filed: May 22, 2018

(86) PCT No.: PCT/IL2018/050554
§ 371 (c)(1),
(2) Date: Nov. 20, 2019

(87) PCT Pub. No.: WO2018/216009
PCT Pub. Date: Nov. 29, 2018

(65) Prior Publication Data
US 2020/0173998 A1   Jun. 4, 2020

Related U.S. Application Data

(60) Provisional application No. 62/509,214, filed on May 22, 2017.

(51) Int. Cl.
C12Q 1/6886 (2018.01)
G01N 33/574 (2006.01)
G01N 33/68 (2006.01)

(52) U.S. Cl.
CPC ..... *G01N 33/57423* (2013.01); *C12Q 1/6886* (2013.01); *G01N 33/6848* (2013.01); *C12Q 2600/158* (2013.01); *G01N 2560/00* (2013.01); *G01N 2800/60* (2013.01)

(58) Field of Classification Search
CPC ............................................... G01N 33/57423
USPC ....................................................... 435/7.23
See application file for complete search history.

(56) References Cited

U.S. PATENT DOCUMENTS

| 4,196,265 | A  | 4/1980  | Croce          |
|-----------|----|---------|----------------|
| 2012/0141603 | A1 | 6/2012  | Tsao           |
| 2012/0178111 | A1 | 7/2012  | Diamandis      |
| 2012/0225954 | A1 | 9/2012  | Moran          |
| 2013/0084287 | A1 | 4/2013  | Shames         |
| 2014/0186837 | A1 | 7/2014  | Shoshan-Barmatz |
| 2016/0032396 | A1 | 2/2016  | Diehn          |
| 2016/0109453 | A1 | 4/2016  | Weinhausel     |
| 2016/0130656 | A1 | 5/2016  | Whitney        |
| 2016/0169900 | A1 | 6/2016  | Kearney        |
| 2016/0263187 | A1 | 9/2016  | Lander         |
| 2016/0319361 | A1 | 11/2016 | Spetzler       |

FOREIGN PATENT DOCUMENTS

| WO | 9522618 A1     | 8/1995  |
|----|----------------|---------|
| WO | 2006113679 A2  | 10/2006 |
| WO | 2010108638 A1  | 9/2010  |
| WO | 2010113172 A1  | 10/2010 |
| WO | 2012149014 A1  | 11/2012 |
| WO | 2013035095 A1  | 3/2013  |
| WO | 2013079215 A1  | 6/2013  |

OTHER PUBLICATIONS

Xie et al (Clin Cancer Res, 2011, 17(17): 5705-5714) teaches.*
Fukuoka et al., Chromatin remodeling factors and BRM/BRG1 expression as prognostic indicators in non-small cell lung cancer, 2004, Clin Cancer Res 10(13): 4314-4324.
Gridelli et al., The potential role of histone deacetylase inhibitors in the treatment of non-small-cell lung cancer. Crit Rev Oncol Hematol, 2008, 68(1): 29-36.
Albertus et al., (2008) AZGP1 autoantibody predicts survival and histone deacetylase inhibitors increase expression in lung adenocarcinoma. J Thorac Oncol 3(11): 1236-1244.
Ao et al., (2014) The utility of a novel triple marker (combination of TTF1, napsin A, and p40) in the subclassification of non-small cell lung cancer. Hum Pathol. Author manuscript; available in PMC Sep. 29, 2014; 17 pages.
Arellano-Llamas et al., (2006) High Smac/DIABLO expression is associated with early local recurrence of cervical cancer. BMC Cancer 6: 256; 10 pages.
Arif et al., (2014) Silencing VDAC1 Expression by siRNA Inhibits Cancer Cell Proliferation and Tumor Growth In Vivo. Mol Ther Nucleic Acids 3: e159; 14 pages.
Arif et al., (2017) VDAC1 is a molecular target in glioblastoma, with its depletion leading to reprogrammed metabolism and reversed oncogenic properties. Neuro Oncol 19(7): 951-964.
Ashburner et al., (2000) Gene ontology: tool for the unification of biology. The Gene Ontology Consortium. Nat Genet 25(1): 25-29.
Bao et al., (2006) Relationship between expression of Smac and Survivin and apoptosis of primary hepatocellular carcinoma. Hepatobiliary Pancreat Dis Int 5(4): 580-583 abstract.
Bar et al., (2008) Multitargeted inhibitors in lung cancer: new clinical data. Clin Lung Cancer 9 Suppl 3: S92-S99.
Battaile et al., (2004) Structures of isobutyryl-CoA dehydrogenase and enzyme-product complex: comparison with isovaleryl- and short-chain acyl-CoA dehydrogenases. J Biol Chem 279(16): 16526-16534.

(Continued)

*Primary Examiner* — Sean E Aeder
(74) *Attorney, Agent, or Firm* — Browdy and Neimark, PLLC

(57) ABSTRACT

The present invention relates to biomarkers of lung cancer, particularly to markers that enable distinguishing between subtypes of non-small cell lung cancer (NSCLC), particularly between adenocarcinoma (AC) and squamous cell carcinoma (SCC). In particular, the present invention relates to means and methods for diagnosing, assessing the level of severity and selecting methods of treating NSCLC.

4 Claims, 9 Drawing Sheets
Specification includes a Sequence Listing.

(56) References Cited

OTHER PUBLICATIONS

Benedettini et al., (2010) Met activation in non-small cell lung cancer is associated with de novo resistance to EGFR inhibitors and the development of brain metastasis. Am J Pathol 177(1): 415-423.

Bing et al., (2004) Zinc-alpha2-glycoprotein, a lipid mobilizing factor, is expressed in adipocytes and is up-regulated in mice with cancer cachexia. Proc Natl Acad Sci U S A 101(8): 2500-2505.

Butler et al., (2011) Modulation of cystatin A expression in human airway epithelium related to genotype, smoking, COPD, and lung cancer. Cancer Res 71(7): 2572-2581.

Campbell et al., (2016) Distinct patterns of somatic genome alterations in lung adenocarcinomas and squamous cell carcinomas. Nat Genet 48(6): 607-616.

Cao et al., (2015) Detection of lung adenocarcinoma with ROS1 rearrangement by IHC, FISH, and RT-PCR and analysis of its clinicopathologic features. Onco Targets Ther 9: 131-138.

Chen et al., (2011) The diagnostic value of cytokeratin 5/6,14, 17, and 18 expression in human non-small cell lung cancer. Oncology 80(5-6): 333-340.

Cheng et al., (2004) The RAB25 small GTPase determines aggressiveness of ovarian and breast cancers. Nat Med 10(11): 1251-1256.

Cheung et al., (2011) Amplification of CRKL Induces Transformation and Epidermal Growth Factor Receptor Inhibitor Resistance in Human Non-Small Cell Lung Cancers. Cancer Discovery 1(7): 608-625.

Chua et al., (2016) TSGΔ154-1054 splice variant increases TSG101 oncogenicity by inhibiting its E3-ligase-mediated proteasomal degradation. Oncotarget 7(7): 8240-8252 with Supplementary Materials.

D'Arena et al., (2006) Rituximab therapy for chronic lymphocytic leukemia-associated autoimmune hemolytic anemia. Am J Hematol 81(8): 598-602.

da Silveira Mitteldorf et al., (2011) FN1, GALE, MMET, and QPCT overexpression in papillary thyroid carcinoma: molecular analysis using frozen tissue and routine fine-needle aspiration biopsy samples. Diagn Cytopathol 39(8): 556-561.

Fahrmann et al., (2016) Proteomic profiling of lung adenocarcinoma indicates heightened DNA repair, antioxidant mechanisms and identifies LASP1 as a potential negative predictor of survival. Clin Proteomics 13: 31; 12 pages.

Falvella et al., (2008) AZGP1 mRNA levels in normal human lung tissue correlate with lung cancer disease status. Oncogene 27(11): 1650-1656.

Fujita et al., (2003) Expression of thyroid transcription factor-1 in 16 human lung cancer cell lines. Lung Cancer 39(1): 31-36.

Fukumoto et al., (2005) Overexpression of the aldo-keto reductase family protein AKR1B10 is highly correlated with smokers' non-small cell lung carcinomas. Clin Cancer Res 11(5): 1776-1785.

Galoian et al., (2014) Lost miRNA surveillance of Notch, IGFR pathway—road to sarcomagenesis. Tumour Biol 35(1): 483-492.

Gene Ontology Consortium (2015) Gene Ontology Consortium: going forward. Nucleic Acids Res 43(Database issue): D1049-D1056.

Grills et al., (2011) Gene expression meta-analysis identifies VDAC1 as a predictor of poor outcome in early stage non-small cell lung cancer. PLoS One 6(1): e14635; 8 pages.

Guryča et al., (2012) Qualitative improvement and quantitative assessment of N-terminomics. Proteomics 12(8): 1207-1216.

Hill et al., (2015) Glycoproteomic comparison of clinical triple-negative and luminal breast tumors. J Proteome Res 14(3): 1376-1388.

Hunt et al., (2002) Characterization of an acyl-coA thioesterase that functions as a major regulator of peroxisomal lipid metabolism. J Biol Chem 277(2): 1128-1138.

Hwang et al., (2015) The Overexpression of FEN1 and RAD54B May Act as Independent Prognostic Factors of Lung Adenocarcinoma. PLoS One 10(10): e0139435; 12 pages.

Janku et al., (2010) Targeted therapy in non-small-cell lung cancer-is it becoming a reality? Nat Rev Clin Oncol 7(7): 401-414.

Jia et al., (2015) Identification of new hub genes associated with bladder carcinoma via bioinformatics analysis. Tumori 101(1): 117-122.

Kawase et al., (2012) Differences between squamous cell carcinoma and adenocarcinoma of the lung: are adenocarcinoma and squamous cell carcinoma prognostically equal? Jpn J Clin Oncol 42(3): 189-195.

Kelstrup et al., (2012) Optimized fast and sensitive acquisition methods for shotgun proteomics on a quadrupole orbitrap mass spectrometer. J Proteome Res 11(6): 3487-3497.

Kempkensteffen et al., (2008) Expression levels of the mitochondrial IAP antagonists Smac/DIABLO and Omi/HtrA2 in clear-cell renal cell carcinomas and their prognostic value. J Cancer Res Clin Oncol 134(5): 543-550.

Kenfield et al., (2008) Comparison of aspects of smoking among the four histological types of lung cancer. Tob Control 17(3): 198-204.

Kim et al., (2013) Best immunohistochemical panel in distinguishing adenocarcinoma from squamous cell carcinoma of lung: tissue microarray assay in resected lung cancer specimens. Ann Diagn Pathol 17(1): 85-90.

Kroemer et al., (2007) Mitochondrial membrane permeabilization in cell death. Physiol Rev 87(1): 99-163.

Lay et al., (2000) Phosphoglycerate kinase acts in tumour angiogenesis as a disulphide reductase. Nature 408(6814): 869-873.

Lee et al., (2016) Identification of a novel partner gene, KIAA1217, fused to RET: Functional characterization and inhibitor sensitivity of two isoforms in lung adenocarcinoma. Oncotarget 7(24): 36101-36114 with Supplementary Materials.

Lee et al., (2016) Genetic polymorphisms in glycolytic pathway are associated with the prognosis of patients with early stage non-small cell lung cancer. Sci Rep 6: 35603; 10 pages.

Leinonen et al., (2007) Biological and prognostic role of acid cysteine proteinase inhibitor (ACPI, cystatin A) in non-small-cell lung cancer. J Clin Pathol 60(5): 515-519.

Li et al., (2016) Mitochondria-Translocated PGK1 Functions as a Protein Kinase to Coordinate Glycolysis and the TCA Cycle in Tumorigenesis. Mol Cell 61(5): 705-719 with Supplemental Information.

Lu et al., (2009) Identification of ATP synthase beta subunit (ATPB) on the cell surface as a non-small cell lung cancer (NSCLC) associated antigen. BMC Cancer 9: 16; 8 pages.

Marchi and Pinton (2014) The mitochondrial calcium uniporter complex: molecular components, structure and physiopathological implications. The Journal of Physiology 592(5): 829-839.

Marusyk and Polyak (2010) Tumor heterogeneity: causes and consequences. Biochim Biophys Acta 1805(1): 105-117.

McCauliff et al., (2015) Multiple Surface Regions on the Niemann-Pick C2 Protein Facilitate Intracellular Cholesterol Transport. J Biol Chem 290(45): 27321-27331 with Supplementary Materials.

Meldrum et al., (2011) Next-generation sequencing for cancer diagnostics: a practical perspective. Clin Biochem Rev 32(4): 177-195.

Miao et al., (2013) Lactate dehydrogenase A in cancer: a promising target for diagnosis and therapy. IUBMB Life 65(11): 904-910.

Min et al., (2012) Expression of HAT1 and HDAC1, 2, 3 in Diffuse Large B-Cell Lymphomas, Peripheral T-Cell Lymphomas, and NK/T-Cell Lymphomas. Korean J Pathol 46(2): 142-150.

Mitsudomi and Yatabe (2007) Mutations of the epidermal growth factor receptor gene and related genes as determinants of epidermal growth factor receptor tyrosine kinase inhibitors sensitivity in lung cancer. Cancer Sci 98(12): 1817-1824.

Nakamura et al., (2007) c-Met activation in lung adenocarcinoma tissues: an immunohistochemical analysis. Cancer Sci 98(7): 1006-1013.

Nakanishi et al., (2013) Semi-nested real-time reverse transcription polymerase chain reaction methods for the successful quantitation of cytokeratin mRNA expression levels for the subtyping of non-small-cell lung carcinoma using paraffin-embedded and microdissected lung biopsy specimens. Acta Histochem Cytochem 46(2): 85-96.

Nawarak et al., (2009) Proteomics analysis of A375 human malignant melanoma cells in response to arbutin treatment. Biochim Biophys Acta 1794(2): 159-167.

(56) References Cited

OTHER PUBLICATIONS

Ogawa et al., (2000) Expression of thrombomodulin in squamous cell carcinoma of the lung: its relationship to lymph node metastasis and prognosis of the patients. Cancer Lett 149(1-2): 95-103.

Ozawa et al., (1999) 150-kDa oxygen-regulated protein (ORP150) suppresses hypoxia-induced apoptotic cell death. J Biol Chem 274(10): 6397-6404.

Paez et al., (2004) EGFR mutations in lung cancer: correlation with clinical response to gefitinib therapy. Science 304(5676): 1497-1500.

Paul et al., (2018) A New Role for the Mitochondrial Pro-apoptotic Protein SMAC/Diablo in Phospholipid Synthesis Associated with Tumorigenesis. Mol Ther 26(3): 680-694 with Supplemental Information.

Pernemalm et al., (2009) Use of narrow-range peptide IEF to improve detection of lung adenocarcinoma markers in plasma and pleural effusion. Proteomics 9(13): 3414-3424.

Pieterman et al., (2000) Preoperative staging of non-small-cell lung cancer with positron-emission tomography. N Engl J Med 343(4): 254-261.

Plönes et al., (2016) Molecular Pathology and Personalized Medicine: The Dawn of a New Era in Companion Diagnostics—Practical Considerations about Companion Diagnostics for Non-Small-Cell-Lung-Cancer. J Pers Med 6(1). pii: E3; 14 pages.

Puzone et al., (2013) Glyceraldehyde-3-phosphate dehydrogenase gene over expression correlates with poor prognosis in non small cell lung cancer patients. Mol Cancer 12(1): 97; 8 pages.

Qin et al., (2012) Smac: Its role in apoptosis induction and use in lung cancer diagnosis and treatment. Cancer Lett 318(1): 9-13.

Saito et al., (2018) Treatment of lung adenocarcinoma by molecular-targeted therapy and immunotherapy. Surg Today 48(1): 1-8.

Sellmann et al., (2015) Improved overall survival following tyrosine kinase inhibitor treatment in advanced or metastatic non-small-cell lung cancer—the Holy Grail in cancer treatment? Transl Lung Cancer Res 4(3): 223-227.

Sevrioukova (2011) Apoptosis-inducing factor: structure, function, and redox regulation. Antioxid Redox Signal 14(12): 2545-2579.

Shen et al., (2017) ARRB1 enhances the chemosensitivity of lung cancer through the mediation of DNA damage response. Oncol Rep 37(2): 761-767.

Shi et al., (2017) Expression profile, clinical significance, and biological function of insulin-like growth factor 2 messenger RNA-binding proteins in non-small cell lung cancer. Tumour Biol 39(4): 1010428317695928; 11 pages.

Shibata et al., (2007) Disturbed expression of the apoptosis regulators XIAP, XAF1, and Smac/DIABLO in gastric adenocarcinomas. Diagn Mol Pathol 16(1): 1-8.

Shoshan-Barmatz et al., (2015) The mitochondrial voltage-dependent anion channel 1 in tumor cells. Biochim Biophys Acta 1848(10 Pt B): 2547-2575.

Shoshan-Barmatz et al., (2017) A molecular signature of lung cancer: potential biomarkers for adenocarcinoma and squamous cell carcinoma. Oncotarget 8(62): 105492-105509 with Supplementary Materials.

Song et al., (2014) Rule discovery and distance separation to detect reliable miRNA biomarkers for the diagnosis of lung squamous cell carcinoma. BMC Genomics 15(Suppl 9): S16; 11 pages.

Steffan et al., (2014) Supporting a role for the GTPase Rab7 in prostate cancer progression. PLoS One 9(2): e87882; 11 pages.

Subramanian and Govindan (2007) Lung cancer in never smokers: a review. J Clin Oncol 25(5): 561-570.

Szász et al., (2016) Cross-validation of survival associated biomarkers in gastric cancer using transcriptomic data of 1,065 patients. Oncotarget 7(31): 49322-49333.

Tainsky (2009) Genomic and proteomic biomarkers for cancer: a multitude of opportunities. Biochim Biophys Acta 1796(2): 176-193.

Tan et al., (2013) Epigenomic analysis of lung adenocarcinoma reveals novel DNA methylation patterns associated with smoking. Onco Targets Ther 6: 1471-1479 with Supplemental Information.

Tang et al., (2015) Epigenetic regulation of Smad2 and Smad3 by profilin-2 promotes lung cancer growth and metastasis. Nat Commun 6: 8230; 15 pages.

Tolnay et al., (1997) Expression and localization of thrombomodulin in preneoplastic bronchial lesions and in lung cancer. Virchows Arch 430(3): 209-212.

Tomasetti et al., (2017) Stem cell divisions, somatic mutations, cancer etiology, and cancer prevention. Science 355(6331): 1330-1334.

Tran (2013) A novel method for finding non-small cell lung cancer diagnosis biomarkers. BMC Med Genomics 6 Suppl 1: S11; 10 pages.

Ueda et al., (2011) A comprehensive peptidome profiling technology for the identification of early detection biomarkers for lung adenocarcinoma. PLoS One 6(4): e18567; 12 pages.

Vander Heiden and DeBerardinis (2017) Understanding the Intersections between Metabolism and Cancer Biology. Cell 168(4): 657-669.

Vargas and Harris (2016) Biomarker development in the precision medicine era: lung cancer as a case study. Nat Rev Cancer 16(8): 525-537.

Vesselle et al., (2007) Fluorodeoxyglucose uptake of primary non-small cell lung cancer at positron emission tomography: new contrary data on prognostic role. Clin Cancer Res 13(11): 3255-3263.

Vogt et al., (2014) p40 (ΔNp63) is more specific than p63 and cytokeratin 5 in identifying squamous cell carcinoma of bronchopulmonary origin: a review and comparative analysis. Diagn Cytopathol 42(5): 453-458.

Wang et al., (2015) RAB34 was a progression- and prognosis-associated biomarker in gliomas. Tumour Biol 36(3): 1573-1578.

Wasylyk et al., (2010) Tubulin tyrosine ligase like 12 links to prostate cancer through tubulin posttranslational modification and chromosome ploidy. Int J Cancer 127(11): 2542-2553.

Xue et al., (2014) RNAi screening identifies HAT1 as a potential drug target in esophageal squamous cell carcinoma. Int J Clin Exp Pathol 7(7): 3898-3907.

Yoo et al., (2003) Immunohistochemical analysis of Smac/DIABLO expression in human carcinomas and sarcomas. APMIS 111(3): 382-388.

Yoshida et al., (2016) Molecular Factors Associated with Pemetrexed Sensitivity According to Histological Type in Non-small Cell Lung Cancer. Anticancer Res 36(12): 6319-6326.

Zakowski et al., (2016) Morphologic Accuracy in Differentiating Primary Lung Adenocarcinoma From Squamous Cell Carcinoma in Cytology Specimens. Arch Pathol Lab Med 140(10): 1116-1120 with Supplemental Information.

Zhu et al., (2016) Function of Deubiquitinating Enzyme USP14 as Oncogene in Different Types of Cancer. Cell Physiol Biochem 38(3): 993-1002.

\* cited by examiner

BIOMARKERS FOR DIAGNOSIS OF LUNG CANCER

FIELD OF THE INVENTION

The present invention relates to biomarkers of lung cancer, particularly to markers that enable distinguishing between subtypes of non-small cell lung cancer (NSCLC), particularly between adenocarcinoma (AC) and squamous cell carcinoma (SCC). In particular, the present invention relates to compositions and methods for diagnosing, assessing the level of severity and treating of NSCLC.

BACKGROUND OF THE INVENTION

Non-small cell lung cancer (NSCLC) is the most prevalent form of lung cancer and represents the leading cause of cancer deaths worldwide in both men and women. Because the majority of diagnosed NSCLC patients are in advanced stages of the disease, overall survival after standard treatment with platinum-based chemotherapy, radiation, and/or surgery remains less than 12 months. Median overall survival can, however, be increased by novel strategies implementing immunotherapies in different combinations; or if a driver mutation exists, then median overall survivable can be increased to four years by targeted tyrosine kinase inhibitory therapy. NSCLC can be divided into a number of sub-types, with the two main sub-types being adenocarcinoma (AC) and squamous cell carcinoma (SCC), together accounting for the vast majority of NSCLC cases (representing almost 80% of primary lung cancer cases) and being responsible for 30% of all cancer deaths. Specifically, AC is the most prevalent subtype of lung cancer in non-smokers, and constitutes approximately 50% of all cases of lung cancer types. In AC, the tumor develops from glandular cells of the lungs that are responsible for producing mucin and surfactants, located at the periphery of the lung. SCC, which constitutes approximately 30% of NSCLC cases, usually develops in central areas of the bronchi of the lung and is closely connected with smoking. Although these two NSCLC sub-types have both unique and shared clinical presentations and histopathological characteristics, the need for genetic investigations and treatment strategy may differ significantly. To insure proper treatment strategy, it is therefore, crucial to be able to distinguish the two NSCLC sub-types during diagnosis (Janku F, et al. Nat Rev Clin Oncol 2010; 7:401-14; Kawase A, et al. Jpn J Clin Oncol 2012; 42:189-95). Current histological discrimination is based on tissue availability, wherein about 15-20% of the cases, tissue is exhausted before final histology can be defined, or as many as 7.2% are poorly differentiated and present not otherwise specified NSCLC. Lung cancer, as many other cancers, develops via a multistep process of tumor biogenesis involving accumulation of inherited or acquired genetic abnormalities (Tomasetti C, et al. Science. 2017; 355:1330-4). These can be detected by deep sequencing methods (Meldrum C, et al. Clin Biochem Rev 2011; 32:177-95), yet it is complicated by the heterogeneity and complexity of malignant tumors (Marusyk A, et al.— Biochim Biophys Acta. 2010; 1805:105-17). However, other cancer-associated changes are not mutation-related but rather appear as an increase or a decrease in protein expression or as differential post-translational modification of marker proteins (Tainsky M A. Biochim Biophys Acta 2009; 1796:176-93). Thus, biomarkers other than mutations should be identified and explored as early markers of the disease, as indicators of the disease state, and as predictive and prognostic measures of treatment effectiveness (Tainsky 2009, ibid).

Recent efforts have focused on changes that occur within the genome, epigenome, transcriptome, and proteome in lung AC and SCC that could serve to distinguish between these two NSCLC sub-types (Campbell J D, et al. Nat Genet 2016; 48:607-16). Currently about 17 biomarkers were reported to be differentially expressed in AC and SCC (Table 1 hereinbelow). Of these, 11 biomarkers are reported to detect AC while only 5 biomarkers are proposed for diagnosing SCC. Currently 4 markers are in use in the clinic to distinguish between the two subtypes and 6 are used to direct targeted therapy (Table 1). Among them are microRNAs, with miR21 being detected in AC while miR205 being associated with SCC (Campbell 2016, ibid). TTF1 (thyroid transcription factor 1), NAPSA (napsin A) and CD141 (Thrombomodulin) were found to be highly expressed in AC as compared to SCC, while high expression levels of TP63 (tumor protein 63) and its isoform p40 (ΔNp63) were reported as markers for SCC (Kim M J, et al. Ann Diagn Pathol 2013; 17:85-90).

There remains an unmet need for adequate biomarkers that are suitable as diagnostic tools for assessing the presence or absence NSCLC, and, more importantly, for distinguishing between the major subtypes of this cancer, AC and SCC.

SUMMARY OF THE INVENTION

The present invention relates to novel biomarkers that are differentially expressed in non-small cell lung cancer (NSCLC) and to biomarkers that are differentially expressed in the NSCLC sub-types adenocarcinoma (AC) and squamous cell carcinoma (SCC), and thus can be used to distinguish between these NSCLC subtypes.

The present invention is based in part on the unexpected discovery that certain proteins show different expression patterns and/or levels of expression in SCC compared to AC.

According to certain aspects the present invention discloses that the expression of each of the proteins and/or mRNA encoding the proteins HAT1 (Histone acetyltransferase type B); LRRFIP2 (Leucine-rich repeat flightless-interacting protein 2); AKR1B10 (Aldo-keto reductase family 1 member B10, a secreted protein); WDR82 (WD repeat-containing protein 82); TTLL12 (Tubulin-tyrosine ligase-like protein 12); IGF2BP3 (Insulin-like growth factor 2 mRNA-binding protein); SMC2 (Structural maintenance of chromosomes protein 2); and ITGA7 (Integrin alpha-7) is higher in tumor samples obtained from patients diagnosed as having NSCLC subtype SCC compared to the expression in samples obtained from patients diagnosed to have the AC subtype.

According to certain aspects, the present invention further discloses that the expression of each of the proteins and/or mRNA encoding the proteins ACAD8 (Isobutyryl-CoA dehydrogenase); TSG101 (Tumor susceptibility gene 101 protein); RAB34 (Ras-related protein Rab-34); RSU1 (Ras suppressor protein); ACOT1 (Acyl-coenzyme A thioesterase 1); GALE (UDP-glucose 4-epimerase); and HYOU1 (Hypoxia up-regulated protein 1) is higher in tumor samples obtained from patients diagnosed as having AC compared to their expression in samples obtained from patients diagnosed for SCC.

According to other aspects, the protein SMAC/Diablo (second mitochondria-derived activator of caspase/direct inhibitor of apoptosis-binding protein with low pI) has been found to be predominantly located in the mitochondria and cytosol in samples obtained from patient diagnosed with AC, while in those diagnosed for SCC, SMAC/Diablo was found to be located not only in the mitochondria and cytosol but about 50% was located in the nucleus.

The present invention also provide newly identified biomarkers (proteins and/or mRNA) of NSCLC, that are highly expressed in samples obtained from cancerous lung tissues of patients diagnosed for NSCLC compared to healthy tissues obtained from the same subject. The novel biomarkers include, but are not limited to, APOOL (Apolipoprotein O-like); VPS29 (Vacuolar protein sorting-associated protein 29); and CAF17 (Iron-sulfur cluster assembly factor homolog), hitherto not known to be associated with cancer.

The present invention thus provides methods and kits for diagnosing NSCLC and for differentiating between the NSCLC subtypes SCC and AC. The present invention further provides masrkers and marker combinations assisting in determining the severity of NSCLC subtype AC. The markers of the invention, alone or in combination with additional markers, may assist in early diagnosis of the disease and/or its subtype, and enable selecting the proper therapy as early as possible. Several markers of the invention and additional markers According to one aspect, the present invention provides a method for diagnosing a subtype of non small cell lung carcinoma (NSCLC) selected from adenocarcinoma (AC) and squamous cell carcinoma (SCC) in a subject suspected to have NSCLC, the method comprising:
 (a) determining the expression level of at least one biomarker selected from a protein and mRNA encoding said protein in a biological sample obtained from the subject, wherein the at least one biomarker is selected from the group consisting of HAT1, LRRFIP2, AKR1B10, WDR82, TTL12, IGF2BP3, SMC2, ACAD8, RSU1, ACOT1, HYOU1, GALE, ITGA7, TSG101, and RAB34;
 (b) comparing the expression level of said at least one biomarker to the expression level of said at least one biomarker in a healthy biological sample and/or a reference value representing healthy biological sample; optionally
 (c) computing a fold change of the expression level of said at least one biomarker in the sample obtained from said subject and the expression level in the healthy sample and/or reference value; and
 (d) diagnosing said subject, wherein—
  an elevated expression level in said sample obtained from said subject of at least one biomarker selected from the group consisting of HAT1, LRRFIP2, AKR1B10, WDR82, TTL12, IGF2BP3, and SMC2, and/or reduced expression of at least one biomarker selected from the group consisting of ACAD8, RSU1, ACOT1, HYOU1, and GALE compared to the expression level in said healthy biological sample and/or reference value indicates that said subject has NSCLC subtype SCC;
  a reduced expression level in said sample obtained from said subject of at least one biomarker selected from the group consisting of HAT1, LRRFIP2, AKR1B10, WDR82, TTL12, IGF2BP3, and SMC2, and/or elevated expression of at least one biomarker selected from the group consisting of ACAD8, RSU1, ACOT1, HYOU1, and GALE compared to the expression level in said healthy biological sample and/or reference value indicates that said subject has NSCLC subtype AC;
  an equal or elevated fold change of the biomarker ITGA7 compared to a reference value indicates that the subject has NSCLC subtype SCC, wherein the reference value is derived from the fold change of the expression of said ITGA7 biomarker in a plurality of samples obtained from SCC patients compared to its expression in a plurality of healthy biological samples;
  an equal or elevated fold change of the biomarker TSG101 compared to a reference value indicates that the subject has NSCLC subtype AC, wherein the reference value is derived from the fold change of the expression of said TSG101 biomarker in a plurality of samples obtained from AC patients compared to its expression in a plurality of healthy biological samples;
  an equal or reduced fold change of the biomarker RAB34 compared to a reference value indicates that the subject has NSCLC subtype AC, wherein the reference value is derived from a fold change of the expression of said RAB34 biomarker in a plurality of samples obtained from AC patients compared to its expression in a plurality of healthy biological samples.

According to certain embodiments, the method comprises determining the expression level of a combination of biomarkers, the combination is selected from the group consisting of at least 2, at least 3, at least 4, at least 5, at least 6, at least 7, at least 8, at least 9, at least 10, at least 11, at least 12, at least 13, at least 14, and 15 biomarkers.

According to certain embodiments, the method comprises determining the expression level of at least one biomarker selected from the group consisting of HAT1, LRRFIP2, AKR1B10, WDR82, TTL12, IGF2BP3, and SMC2, and at least one biomarker selected from the group consisting of ACAD8, RSU1, ACOT1, HYOU1, and GALE. Each possibility represents a separate embodiment of the present invention.

According to certain embodiments, the method comprises determining the expression level of at least one biomarker selected from the group consisting of HAT1, LRRFIP2, AKR1B10, WDR82, TTL12, IGF2BP3, SMC2, and ITGA7 and at least one biomarker selected from the group consisting of ACAD8, RSU1, ACOT1, HYOU1, GALE, TSG101 and RAB34.

According to certain embodiments, the method comprises determining the expression level of a combination of markers, the combination comprises the biomarkers HAT1, LRRFIP2, AKR1B10, WDR82, TTL12, IGF2BP3, and SMC2.

According to certain embodiments, the method comprises determining the expression level of a combination of markers, the combination comprises the biomarkers ACAD8, RSU1, ACOT1, HYOU1, and GALE.

According to certain embodiments, the method comprises determining the expression level of a combination of markers, the combination comprises the biomarkers HAT1, LRRFIP2, AKR1B10, WDR82, TTL12, IGF2BP3, SMC2, ITGA7, ACAD8, RSU1, ACOT1, HYOU1, GALE, TSG101 and RAB34.

According to certain embodiments, the method comprises determining the expression level of at least two biomarkers, said method further comprises determining the expression level of at least one of USP14 (Ubiquitin carboxyl terminal hydrolase 14), VDAC1 (voltage-dependent anion channel-1) and AIF (Apoptosis inducing factor), wherein an equal or elevated fold change of the at least one biomarker compared to a reference value indicates that the subject has NSCLC subtype SCC, wherein the reference value is derived from the fold change of the expression of said at least one biomarker in a plurality of samples obtained from SCC patients compared to the expression in a plurality of healthy biological samples.

According to certain embodiments, the expression level of the at least one biomarker is at least 2 fold, at least 3, fold, at least 4 fold, at least 5 fold, at least 10 fold, at least 50 fold, at least 100 fold, at least 500 fold, at least 1,000 fold and more higher or lower compared to the expression of said biomarker in the healthy sample or to the reference value.

According to certain exemplary embodiments, expression level of the at least one biomarker is at least 4 fold higher compared to the expression of said biomarker in the healthy sample or reference value.

According to certain embodiments, the biological marker is a protein.

According to certain exemplary embodiments, the biological sample is a lung tissue sample. According to these embodiments, the healthy biological sample is obtained from a healthy subject or from a healthy lung tissue of the subject suspected to have NSCLC.

According to certain embodiments, the biomarker is a secreted protein and the biological sample is selected from the group consisting of blood sample, blood plasma sample and serum sample. According to some embodiments, the biological sample obtained from the subject is ascite.

According to certain embodiments, the method further comprises treating the subject diagnosed to have NSCLC subtype AC with a therapy suitable for treating AC.

Any therapy known to be effective in treating NSCLC subtype AC can be used according to the teachings of the present invention.

According to some embodiments, the therapy suitable for treating AC comprises administering to the subject a therapeutically effective amount of at least one agent that reduces the expression or activity of at least one protein selected from the group consisting of TSG101, ACAD8, and GALE. Each possibility represents a separate embodiment of the present invention.

According to certain embodiments, the method further comprises treating the subject diagnosed to have NSCLC subtype SCC with a therapy suitable for treating SCC.

Any therapy known to be effective in treating NSCLC subtype SCC can be used according to the teachings of the present invention.

According to some embodiments, the therapy suitable for treating SCC comprises administering to the subject a therapeutically effective amount of at least one agent that reduces the expression or activity of at least one protein selected from the group consisting of HAT1, LRRFIP2, AKR1B10, WDR82, TTL12, IGF2BP3, and ITGA7. Each possibility represents a separate embodiment of the present invention.

According to certain embodiments, the agent that reduces the expression or activity of the at least one protein is selected from the group consisting of a chemical agent or moiety, a protein, a peptide, and a polynucleotide molecule. Each possibility represents a separate embodiment of the present invention.

According to certain embodiments, the agent is an antibody.

According to certain exemplary embodiments, the agent is an interfering RNA (RNAi) molecule selected from the group consisting of shRNA, siRNA, and miRNA.

According to yet additional aspect, the present invention provides a method for diagnosing a subtype of non small cell lung carcinoma (NSCLC) selected from the group consisting of squamous cell carcinoma (SCC) and adenocarcinima (AC) in a subject suspected to have NSCLC, the method comprises (a) determining the presence of SMAC/Diablo protein in a cell-comprising sample obtained from the subject and (b) diagnosing said subject as having NSCLC subtype SCC when a significant amount of the SMAC/Diablo protein is present in the cell nucleus and in the cell cytosol and as having NSCLC subtype AC when no significant amount of said SMAC/Diablo protein is present in the cell nucleus and a significant amount is present in the cytosol.

According to certain embodiments, the method further comprises treating the subject diagnosed to have NSCLC subtype AC with a therapy suitable for treating AC.

According to certain embodiments, the method further comprises treating the subject diagnosed to have NSCLC subtype SCC with a therapy suitable for treating SCC. The methods for treating AC or SCC are as known in the art and as described hereinabove.

According to yet further aspect, the present invention provides a method for diagnosing NSCLC in a subject, the method comprising:
  (a) comparing the expression level of at least one biomarker selected from a protein or mRNA encoding the protein in a biological sample of the subject to a control biological sample or reference value, wherein the at least one biomarker is selected from the group consisting of APOOL, VPS29, CAF17, and any combination thereof;
  (b) diagnosing the subject as having NSCLC wherein the expression level of said at least one biomarker or of a combination of the biomarkers is increased compared to the expression in the control biological sample or to the reference value.

According to certain embodiments, the method for diagnosing NSCLC comprises comparing the expression level of at least two biomarkers or of the three biomarkers. According to certain embodiments, the method further comprises comparing the expression level of at least one additional biomarker selected from the biomarkers set fort in Table 2 hereinbelow.

According to certain exemplary embodiments, the method for diagnosing NSCLC further comprises comparing the expression level at least one additional biomarker selected from the group consisting of VDAC1, AIF, ATP5B, HSp60, GADPH, PGK1, ENO1, LDHA and Rab11B. Each possibility represents a separate embodiment of the present invention.

According to certain exemplary embodiments, the additional marker is selected from PGK1 and Rab11.

According to certain embodiments, the biological sample is a lung tissue. According to these embodiments, the control sample is obtained from a healthy subject.

According to certain embodiments, the reference value represents a statistical measure representing the expression level of each of the biomarkers in a plurality of samples obtained from a plurality of healthy subjects.

According to certain embodiments, expression level of the at least one biomarker is at least 2 fold, at least 3, fold, at least 4 fold, at least 5 fold, at least 10 fold, at least 50 fold, at least 100 fold, at least 500 fold, at least 1,000 fold and more higher compared to the expression of said biomarker in the healthy sample or reference value. According to certain exemplary embodiments, expression level of the at least one biomarker is at least 4 fold higher compared to the expression of said biomarker in the healthy sample or to the reference value.

According to certain embodiments, the at least one biomarker is a protein.

According to certain embodiments, the method of diagnosing a subject as having NSCLC further comprises treating said subject with a therapy suitable for treating NSCLC. Therapies for treating NSCLC are known in the art. According to some embodiments, treating the NSCLC comprises administering to the subject a therapeutically effective amount of at least one agent that reduces the expression or activity of at least one protein selected from the group consisting of APOOL, VPS29, and CAF17.

Agents that reduce the expression of the at least one biomarkers are as known in the art and as described hereinabove.

According to additional aspect, the present invention provides a method for predicting the severity of NSCLC subtype AC, the method comprising:
(a) comparing the expression level of at least one biomarker selected from a protein and mRNA encoding said protein in a biological sample obtained from a subject diagnosed to have NSCLC subtype AC to a reference value, wherein the at least one biomarker is selected from the group consisting of: VDAC1, SMAC, HYOU1, TTLL12, RAB34, ARL1, HAT1, p40, NAPSA LRRFIP2, AIF, TITF, WDR82 and TSG101;
(b) predicting the level of severity of the disease, wherein an increase in the level of at least one biomarker selected from the group consisting of VDAC1, SMAC, HYOU1, TTLL12, and RAB34 compared to the reference value characterizes said patient as having a severe form of the disease; and wherein an increase in the level of at least one biomarker selected from the group consisting of ARL1, HAT1, p40, NAPSA LRRFIP2, AIF, TITF, WDR82 and TSG101 compared to the reference value characterizes said patient as having a milder form of the disease.

According to certain embodiments, a milder form of the disease indicates a longer survival rate compared to the severe form.

According to certain embodiments, the biomarker is an mRNA marker.

According to certain embodiments of the present invention, comparing the expression level of at least one protein biomarker or mRNA encoding same in a biological sample of the subject to a reference value comprises determining the expression level of the at least one protein biomarker or mRNA encoding same in the sample and comparing said expression level to the reference value. According to additional embodiments, comparing the expression level of at least one protein or mRNA biomarker in a biological sample of the subject to a control sample comprises determining the expression level of the at least one protein or mRNA biomarker in the sample obtained from said subject and in the control sample and comparing said determined levels.

According to certain embodiments, the sample is a tissue sample. According to certain embodiments, the control sample is a tissue taken from a healthy subject or subject(s). According to certain exemplary embodiments, for differentiating between the NSCLC subtypes, the sample to be analyzed is a tumor tissue taken from a subject and the control tissue is a healthy tissue taken from the same subject. According to yet additional embodiments, the control tissue is taken from subject(s) diagnosed for NSCLC subtype SCC or subtype AC.

According to yet another aspect, the present invention provides a method for treating NSCLC subtype SCC, the method comprises administering to a subject in need thereof a therapeutically effective amount of at least one agent that reduces the expression or activity of at least one protein selected from the group consisting of HAT1, LRRFIP2, AKR1B10, WDR82, TTLL12, ITGA7, IGF2BP3, and USP14.

According to yet additional aspect, the present invention provides a method for treating NSCLC subtype AC, the method comprises administering to a subject in need thereof, a therapeutically effective amount of at least one agent that reduces the expression or activity of at least one protein selected from the group consisting of ACAD8, TSG101, and GALE.

According to yet further aspect, the present invention provides a method for treating NSCLC, the method comprises administering to a subject in need thereof, a therapeutically effective amount of at least one agent that reduces the expression or activity of at least one protein selected from the group consisting of APOOL, VPS29, and CAF17.

Any agent as is known in the art and as described hereinabove that can reduce the expression or activity of the biomarker can be used according to the teachings of the invention.

According to additional aspect, the present invention provides a kit for diagnosing a subtype of non-small cell lung carcinoma (NSCLC) selected from adenocarcinoma (AC) and squamous cell carcinoma (SCC) in a biological sample obtained from a subject suspected to have NSCLC, the kit comprising:
(a) at least one agent capable of detecting the expression level of at least one biomarker selected from a protein and mRNA encoding said protein, the biomarker is selected from the group consisting of HAT1, LRRFIP2, AKR1B10, WDR82, TTL12, IGF2BP3, SMC2, ACAD8, RSU1, ACOT1, HYOU1, GALE, ITGA7, TSG101, and RAB34;
(b) means for comparing the expression level of the at least one biomarker to a first reference value derived from the expression of the at least one biomarker in healthy biological sample and/or to a second reference value derived from the fold change of the expression of said at least one biomarker in a plurality of samples obtained from SCC patients compared to the expression in a plurality of healthy biological samples; and/or to a third reference value derived from a fold change of the expression of the at least one biomarker in a plurality of samples obtained from AC patients compared to a plurality of healthy biological samples;
(c) instruction material providing guidance to the correlation of said expression level of said at least one biomarker with the NSCLC subtype, wherein:
an increased expression level in said sample of at least one biomarker selected from the group consisting of HAT1, LRRFIP2, AKR1B10, WDR82, TTL12, IGF2BP3, and SMC2, and/or reduced expression of at least one biomarker selected from the group consisting of ACAD8, RSU1, ACOT1, HYOU1, and GALE compared to the first reference value indicates that said subject has NSCLC subtype SCC;
a reduced expression level in the sample of at least one biomarker selected from the group consisting of HAT1, LRRFIP2, AKR1B10, WDR82, TTL12, IGF2BP3, and SMC2, and/or elevated expression of at least one biomarker selected from the group consisting of ACAD8, RSU1, ACOT1, HYOU1, and GALE compared to the first reference value indicates that said subject has NSCLC subtype AC;

an equal or elevated fold change of the biomarker TGA7 compared to the second reference value indicates that the subject has NSCLC subtype SCC;

an equal or elevated fold change of the biomarker TSG101 compared to the third reference value indicates that the subject has NSCLC subtype AC; and/or an equal or reduced fold change of the biomarker RAB34 compared to the third reference value indicates that the subject has NSCLC subtype AC.

According to certain embodiments, the kit further comprises at least one agent capable of detecting the expression of SMAC/Diablo protein within the nucleus of cells present within the biological sample and instruction material providing guidance to correlation of the amount of SMAC/Diablo within the cell nucleus and the cytosol and NSCLC subtype, wherein a significant amount of the SMAC/Diablo protein in the cell nucleus and cytosol diagnose the subject as having NSCLC subtype SCC and no significant amount of said SMAC/Diablo protein in the cell nucleus while a significant amount is present in the cytosol diagnose the subject as having NSCLC subtype AC.

According to yet additional aspect, the present invention provides a kit for diagnosing NSCLC, the kit comprising:
(a) at least one agent capable of detecting the expression level of at least one biomarker selected from a protein and mRNA encoding said protein, the biomarker is selected from the group consisting of APOOL, VPS29, and CAF17 in a biological sample of a subject suspected of having NSCLC;
(b) means for comparing the expression level of the at least one biomarker in a control sample obtained from a healthy subject or to a reference value; and
(c) instruction material providing guidance to the correlation of an increase in the expression level of said at least one biomarker compared to the control sample or reference value with NSCLC.

It is to be understood that any combination of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows statistical and functional analysis of protein expression in samples obtained from healthy and tumor samples of patients with lung cancer.

FIG. 2 shows over-expression of VDAC1 and other apoptosis- and energy-related proteins in samples obtained from lung cancer patients.

FIG. 4 shows proteins differentially expressed in AC and SCC.

FIG. 5 shows gene expression as determined by RNAseq of potential protein markers in lung cancer patients.

DETAILED DESCRIPTION OF THE INVENTION

Figure 1A:
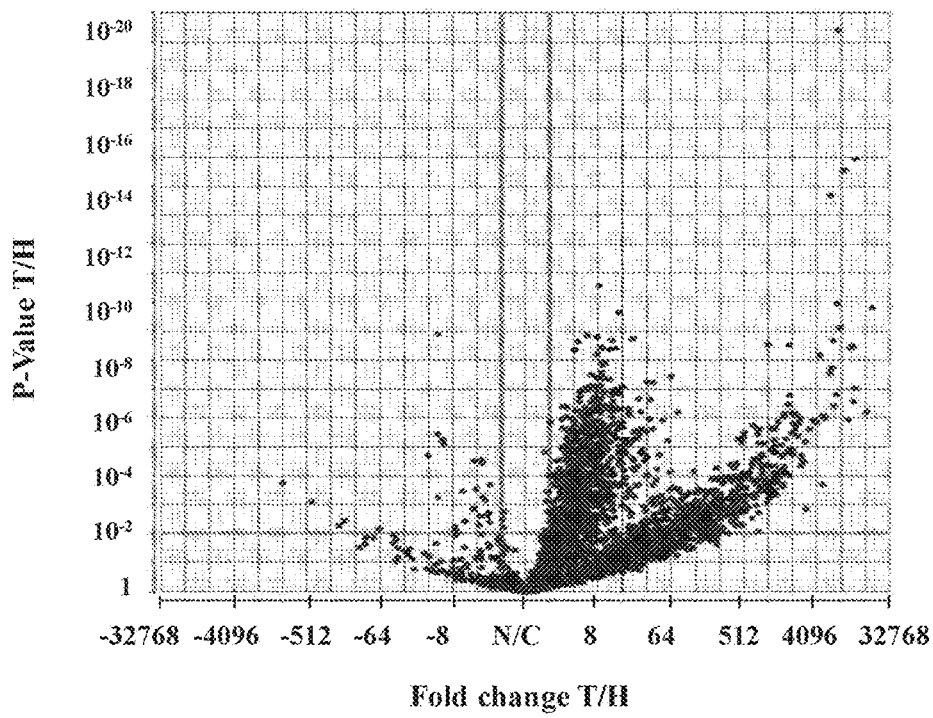
FIG. 1A shows a Volcano plot representing the fold change (X axis) and fold discovery rate (FDR, Y axis) values for each identified protein. Vertical lines indicate fold change >2 or <−2 and horizontal line indicates p-value <0.05. 1,494 proteins passed these thresholds.

Several markers has been previously suggested to be associated with lung cancer, including non-small cell lung carcinoma (NSCLC) and its subtypes, adenocarcinoma (AC) and squamous cell carcinoma (SCC). Several markers proposed to be used in the diagnosis of lung cancer are listed in Table 1. The present invention answers the remaining need for accurate and efficient method for diagnosing NSCLC, particularly for distinguishing between NSCLC subtype SCC and NSCLC subtype AC, which enable selecting an appropriate treatment for each disease subtype based on the diagnosis.

The diagnosis of NSCLC and the differentiation between the NSCLC subtypes SCC and AC is based on differential expression of proteins and/or RNA encoding the proteins in cancerous lung tissue compared to healthy tissue and in SCC cancerous tissues compared to AC cancerous tissues. The diagnosis can be assessed by measuring one or more of the biomarkers described herein. The correct diagnosis, particularly the precise diagnosis of the NSCLC subtype enables the selection and initiation of therapeutic interventions or treatment regimens that are suitable to the disease subtype, in order to delay, reduce, or treat the subject's disease. The diagnosis method of the invention may further provide for early diagnosis of the cancerous disease and/or its subtypes. An early diagnosis is of high importance in increasing the life expectancy of the patient.

The control samples to which the expression level of one or more biomarkers of the invention in a sample obtained from a subject suspected to have NSCLC is compared to are samples taken from healthy subjects or from healthy tissues of subjects suspected to have or affected with lung cancer. The control reference values are also based on samples taken from healthy subject or healthy tissue, or from subjects already diagnosed to have NSCLC, NSCLC subtype AC or NSCLC subtype SCC. Typically, the control reference value is an average or another statistical measure representing the expression level of each of the biomarkers in a plurality of samples. The control and cancerous level and cut-off points may vary based on whether a biomarker is used alone or in a formulae combining with other biomarkers into an index or indices. Alternatively, the normal or abnormal cancerous level can be a database of biomarker patterns or "signatures" from previously tested subjects who did or did not develop NSCLC, NSCLC subtype AC or NSCLC subtype SCC.

One or more clinical parameters may be used in combination with the biomarkers of the present invention as input to a formula or as pre-selection criteria defining a relevant population to be measured using a particular biomarker panel and formula. Clinical parameters may also be useful in the biomarker normalization and pre-processing, or in biomarker selection, formula type selection and derivation, and formula result post-processing.

TABLE 1

Biomarkers proposed for use in diagnosing lung cancer

| | Protein/microRNAs (Uniprot) | Marker for: |
|---|---|---|
| 1 | miR21 | AC (Campbell et al. 2016, ibid). |
| 2 | EGFR- Epidermal growth factor receptor (tyrosine kinase) | Over-expressed in NSCLC (Paez JG, et al. Science. 2004; 304: 1497-500; Mitsudomi T, Yatabe Y. Cancer Sci. 2007; 98: 1817-24) and AC (Saito M, et al. Surgery Today. 2017: 1-8). |
| 3 | ALK-EML4- Tyrosine-protein kinase receptor | AC (Plones T, et al. Journal of Personalized Medicine. 2016; 6: 3; Mitsudomi T, Yatabe Y., 2017, ibid) |
| 4 | ROS1- Proto-oncogene tyrosine-protein kinase ROS | AC (Cao B, et al. OncoTargets and therapy. 2016; 9: 131-8) |
| 5 | RET- Proto-oncogene tyrosine-protein kinase receptor Ret | AC (Lee M-Set al. Oncotarget. 2016; 7: 36101-14). |
| 6 | c-MET -Hepatocyte growth factor receptor (tyrosine kinase) | Over-expressed in NSCLC (Benedettini E, et al. Met Am J Pathol. 2010; 177: 415-23; Nakamura Y, et al. Cancer Sci. 2007; 98: 1006-13). |
| 7 | ERBB2- Receptor tyrosine-protein kinase erbB-2 | AC (Nakamura Y, et al. Cancer Sci. 2007; 98: 1006-13). |
| 8 | PPP3CA- Serine/threonine-protein phosphatase 2B catalytic subunit | AC (Vargas AJ, et al. Nature Reviews Cancer. 2016; 16: 525-37). alpha isoform. (Mutation) |
| 9 | DOT1L- Histone-lysine N-methyltransferase, H3 lysine-79 specific. (Mutated) | AC (Campbell JD, et al. 2016, ibid). |
| 10 | FTSJD1- cap-specific mRNA (nucleoside-2'-0-)-methyltransferase 2. (Mutation) | AC (Campbell JD, et al. 2016, ibid). |
| 11 | TTF1-thyroid transcription factor 1 | AC (Ao MH, et al. Hum Pathol. 2014; 45: 926-34). |
| 12 | NAPSA- napsin A | AC (Ao MH, et al. 2014, ibid) |

TABLE 1-continued

Biomarkers proposed for use in diagnosing lung cancer

| Protein/microRNAs (Uniprot) | Marker for: |
| --- | --- |
| 13 TP63- Tumor protein 63 | SCC (Vogt AP, et al. Diagn Cytopathol. 2014; 42: 453-8). |
| 14 p40- ANp63 | SCC (Ao MH, et al. 2014, ibid; Kim MJ, et al. Ann Diagn Pathol. 2013; 17: 85-90) |
| 15 RASA1- Ras GTPase-activating protein-1 | SCC (Paez JG, et al. 2004, ibid; Mitsudomi T, Yatabe Y. 2007 ibid). |
| 16 CD141- Thrombomodulin | SCC (Ogawa H, et al. Cancer Lett. 2000; 149: 95-103; Tolnay E, et al. Virchows Arch. 1997; 430: 209-12). |
| 17 miR205 | SCC (Campbell JD, et al. 2016, ibid). |

Markers 2 to 6 are predictive markers used to direct targeted therapy and markers 11-14 serve in the clinic for diagnosis of AC or SCC.

Definitions

The term "biomarker" as used herein refers to a protein or gene (particularly RNA, more particularly mRNA) that is differentially expressed in a sample taken from a subject having NSCLC as compared to a sample taken from a healthy subject or in a sample taken from subject having NSCLC subtype SCC in comparison to subject having NSCLC subtype AC or to a healthy subject, or in a sample taken from subject having NSCLC subtype AC in comparison to subject having NSCLC subtype SCC or to a healthy subject.

The term "diagnosing" as used herein means assessing whether a subject suffers from NSCLC or not, and/or whether a subject suffers from NSCLC subtype SCC or NSCLC subtype AC. As will be understood by those skilled in the art, such an assessment is usually not intended to be correct for all (i.e. 100%) of the subjects to be identified. The term, however, requires that a statistically significant portion of subjects can be identified. The term diagnosis also refers, in some embodiments, to screening. Screening for cancer, in some embodiments, can lead to earlier diagnosis in specific cases and diagnosing the correct disease subtype can lead to adequate treatment.

As used herein, the term "level" refers to the degree of gene product expression in the biological sample.

As referred to herein, the term "treating" is directed to ameliorating symptoms associated with a disease, and lessening the severity or cure the disease.

The term "subject" refers to any mammalian subject. In some embodiments, the subject is a human subject.

The term "patient" as used herein refers to a subject that was diagnosed to have NSCLC, NSCLC subtype AC and NSCLC subtype AC.

As used herein, the term "biological sample" refers to a sample obtained from a subject. According to certain typical embodiments, the sample is a biological tissue obtained in vivo or in vitro. Biological samples can be, without limitation, body fluid selected from blood, blood plasma, serum, organs, tissues, fractions and cells isolated from the subject/patient. Biological samples also may include sections of the biological sample including tissues (e.g., sectional portions of an organ or tissue). Biological samples may be dispersed in solution or may be immobilized on a solid support, such as in blots, assays, arrays, glass slides, microtiter, or ELISA plates.

According to one aspect, the present invention provides a method for diagnosing a subtype of non small cell lung carcinoma (NSCLC) selected from adenocarcinoma (AC) and squamous cell carcinoma (SCC) in a subject suspected to have NSCLC, the method comprising:
(a) determining the expression level of at least one biomarker selected from a protein and mRNA encoding said protein in a biological sample obtained from the subject, wherein the at least one biomarker is selected from the group consisting of HAT1, LRRFIP2, AKR1B10, WDR82, TTL12, IGF2BP3, SMC2, ACAD8, RSU1, ACOT1, HYOU1, GALE, ITGA7, TSG101, and RAB34;
(b) comparing the expression level of the at least one biomarker to the expression level of said at least one biomarker in a healthy biological sample and/or a reference value representing healthy biological sample; optionally
(c) computing a fold change of the expression level of said at least one biomarker in the sample obtained from the subject and the expression level in the healthy sample and/or reference value; and
(d) diagnosing said subject, wherein—
an elevated expression level in said sample obtained from said subject of at least one biomarker selected from the group consisting of HAT1, LRRFIP2, AKR1B10, WDR82, TTL12, IGF2BP3, and SMC2, and/or reduced expression of at least one biomarker selected from the group consisting of ACAD8, RSU1, ACOT1, HYOU1, and GALE compared to the expression level in said healthy biological sample and/or reference value indicates that said subject has NSCLC subtype SCC;
a reduced expression level in said sample obtained from said subject of at least one biomarker selected from the group consisting of HAT1, LRRFIP2, AKR1B10, WDR82, TTL12, IGF2BP3, and SMC2, and/or elevated expression of at least one biomarker selected from the group consisting of ACAD8, RSU1, ACOT1, HYOU1, and GALE compared to the expression level in said healthy biological sample and/or reference value indicates that said subject has NSCLC subtype AC;
an equal or elevated fold change of the biomarker ITGA7 compared to a reference value indicates that the subject has NSCLC subtype SCC, wherein the reference value is derived from the fold change of the expression of said ITGA7 biomarker in a plurality of samples obtained from SCC patients compared to the expression in a plurality of healthy biological samples;

an equal or elevated fold change of the biomarker TSG101 compared to a reference value indicates that the subject has NSCLC subtype AC, wherein the reference value is derived from the fold change of the expression of said TSG101 biomarker in a plurality of cancerous samples obtained from AC patients compared to the expression in a plurality of healthy biological samples;

an equal or reduced fold change of the biomarker RAB34 compared to a reference value indicates that the subject has NSCLC subtype AC, wherein the reference value is derived from a fold change of the expression of said RAB34 biomarker in a plurality of cancerous samples obtained from AC patients compared to a plurality of healthy biological samples.

According to certain embodiments, each of the HAT1, LRRFIP2, AKR1B10, WDR82, TTL12, IGF2BP3, SMC2, ACAD8, RSU1, ACOT1, HYOU1, GALE, ITGA7, TSG101, and RAB34 biomarkers is a protein biomarker. According to certain embodiments, each of the HAT1, AKR1B10, WDR82, TTL12, IGF2BP3, SMC2, ACAD8, RSU1, ACOT1, HYOU1, GALE, ITGA7, TSG101, and RAB34 biomarkers is an RNA biomarker.

According to yet additional aspect, the present invention provides a method for diagnosing a subject suspected to have NSCLC for a subtype of NSCLC selected from the group consisting of SCC and AC, the method comprises determining the presence of a SMAC/Diablo protein in a cell-comprising sample obtained from the subject, wherein said subject is diagnosed as having NSCLC subtype SCC when a significant amount of the SMAC/Diablo protein is present in the cell nucleus and in the cell cytosol and as having NSCLC subtype AC when no significant amount of said SMAC/Diablo protein is present in the cell nucleus and a significant amount is present in the cytosol.

According to yet further aspect, the present invention provides a method for diagnosing NSCLC in a subject, the method comprising:
(a) comparing the expression level of at least one protein biomarker or mRNA encoding the protein in a biological sample of the subject to a reference value or a control sample, wherein said at least one biomarker is selected from the group consisting of APOOL; VPS29; CAF17; and any combination thereof;
(b) diagnosing the subject as having NSCLC wherein the expression level of the at least one biomarker or of combination thereof is increased compared to the reference value or control sample.

According to certain embodiments, the method further comprises comparing the expression level of at least one additional biomarker selected from the group presented in Table 2 or mRNA encoding same.

TABLE 2

NSCLC biomarkers

| Protein name (Uniprot) | Fold change/P value | Proposed function (cell localization) | Relation to cancer |
| --- | --- | --- | --- |
| RB11B/Rab11B - Ras-related protein | >1000<br>$7.7 \times 10^{-12}$ | Regulator of intracellular membrane trafficking (Extracellular space, Endosome) | Over-expressed in HL-60 leukemia cell line |
| PIGS - GPI transamidase component PIG-S | >1000<br>$1.3 \times 10^{-9}$ | Component of the GPI transamidase complex (ER) | Over-expressed in breast, ovary and uterus cancers |
| NICA - Nicastrin | >1000<br>$5.8 \times 10^{-9}$ | A subunit of the gamma-secretase complex (Melanosome) | Regulates breast cancer stem cell properties and tumor growth |
| NDKB - Nucleoside diphosphate kinase B | 14.5<br>$3.1 \times 10^{-9}$ | Synthesis of nucleoside triphosphates other than ATP (Cytosol, Nucleus) | High expression reduce metastases in breast cancer, melanoma |
| HNRPL - Heterogeneous nuclear ribonucleoprotein L | 7.3<br>$1.3 \times 10^{-8}$ | Splicing factor, acting as activator or repressor of exon inclusion (Cytosol, Nucleus) | Marker for secondary to brain ALL metastasis |
| STT3A - Dolichyl-diphospho-oligo saccharide-protein glycosyltransferase | 8.3<br>$1.2 \times 10^{-7}$ | Catalytic subunit of the N-oligosaccharyl transferase (OST) complex (ER) | Marker for follicular thyroid carcinoma |
| COPA - Coatomer subunit alpha | 14.6<br>$1.3 \times 10^{-7}$ | Part of a complex that mediates protein transport from the ER to the Golgi, (Cytosol, Golgi) | Associated with mouse mesothelioma progression |
| PDLI5 - PDZ and LIM domain protein 5 | 9.2<br>$1.8 \times 10^{-7}$ | Z-disc protein that interacts directly with a-actinin-2 (Cytosol, Cell junction) | Associated with gastric cancer. High deletion frequencies in oral squamous cell carcinoma. |
| HINT1- Histidine triad nucleotide-binding protein 1 | 5.4<br>$2.0 \times 10^{-7}$ | Hydrolyzes purine nucleotide phosphoramidates (Cytosol, Nucleus) | Over-expressed in prostate cancer |
| SEC11A - Signal peptidase complex catalytic subunit | >1000<br>$2.3 \times 10^{-7}$ | Component of a complex that removes signal peptides from proteins translocated into the ER (ER) | Contributes to malignant progression in gastric cancer |
| DDX6 - DEAD box protein 6 | 62.8<br>$2.5 \times 10^{-7}$ | Participates in mRNA degradation (Cytosol, Nucleus) | Chromosomal aberrations, DDX6 contribute to lymphomagenesis |
| PGK1 - Phosphoglycerate kinase 1 | 8.9<br>$3.2 \times 10^{-7}$ | Glycolytic enzyme, converting 3-phospho-D-glycerate to 3-phospho-D-glyceroyl phosphate (Cytosol) | Prognostic biomarker of poor survival and chemoresistance to paclitaxel treatment in breast cancer |

TABLE 2-continued

NSCLC biomarkers

| Protein name (Uniprot) | Fold change/P value | Proposed function (cell localization) | Relation to cancer |
| --- | --- | --- | --- |
| IF4E - Eukaryotic transition initiation factor 4E | 7.7<br>$3.5 \times 10^{-7}$ | Participates in the initiation of translation (Cytosol) | eIF4E over-expression can initiate malignant transformation |
| GDIB - Rab GDP dissociation inhibitor beta | 4.5<br>$3.9 \times 10^{-7}$ | Regulates the GDP/GTP exchange of most Rab proteins (Cytosol, Plasma membrane) | Increased in metastatic gallbladder cancer cell line SD18H and in pancreatic carcinoma |
| RL9 - 60S ribosomal protein L9 | 21.1<br>$4.5 \times 10^{-7}$ | Translation. Component of the 60S subunit (Cytosol) | Over-expressed in colon adenoma and adenocarcinoma |
| NDUS7 - ADH dehydrogenase (ubiquinone) iron-sulfur protein 7 | >1000<br>$4.7 \times 10^{-7}$ | Core subunit of the respiratory chain NADH dehydrogenase (Mitochondria) | Amplification in BRCA1-associated ovarian cancer |
| PTBP1 - Polypyrimidine tract-binding protein 1 | 8.4<br>$5.1 \times 10^{-7}$ | Plays a role in pre-mRNA splicing (Nucleus) | Over-expressed in colorectal cancer, gemcitabine resistance in pancreatic cancer, associated with breast tumorigenesis |
| PA1B2 - Platelet-activating factor acetyl-hydrolase IB subunit beta | 9.9<br>$5.9 \times 10^{-7}$ | Inactivates PAF (platelet-activating factor) (Cytosol) | Important in maintaining cancer pathogenicity across a wide spectrum of cancer types |
| PPOX - Proto-porphyrinogen oxidase | >1000<br>$6.6 \times 10^{-7}$ | Catalyzes the oxidation of protoporphyrinogen-IX to form protoporphyrin-IX (Mitochondria) | Higher expression in faster growing cell lines and primary colorectal tumors |
| RL10 - 60S ribosomal protein L10a | 7.8<br>$7.1 \times 10^{-7}$ | Translation. Component of the 60S subunit (Cytosol) | Mutated in T-cell acute lymphoblastic leukemia |
| ILF2 - Interleukin enhancer-binding factor 2 | 5.0<br>$7.7 \times 10^{-7}$ | Regulatory subunit of complexes involved in mitotic control, DNA break repair, and RNA splicing regulation (Cytosol Nucleus) | Higher expression in esophageal squamous cell carcinoma |
| UGPA - UTP-glucose-1-phosphate uridylyltransferase | 7.7<br>$9.5 \times 10^{-7}$ | Glucosyl donor in cellular metabolic pathways (Cytosol) | Biomarker for metastatic hepatocellular carcinoma |
| DDX17 - DEAD box protein 17 | 5.6<br>$1.2 \times 10^{-6}$ | RNA helicase, involved in transcription and splicing (Nucleus) | Increased expression in colon cancer |
| OSBL8 - Oxysterol-binding protein-related protein 8 | >1000<br>$1.2 \times 10^{-6}$ | Binds 25-hydroxycholesterol and cholesterol (ER membrane, Nucleus membrane) | Down-regulated in hepatoma tissues |
| TXD12 (ERp19) - Thioredoxin domain-containing protein 12 | 37.6<br>$1.4 \times 10^{-6}$ | Involved in thiol-disulfide oxidase activity (ER) | A thioredoxin-like protein, implicated in development of breast, ovarian, gastrointestinal and gastric cancers |
| USO1 - General vesicular transport factor p115 | 8.7<br>$1.4 \times 10^{-6}$ | General vesicular transport factor in Golgi (Cytosol, Golgi) | Promotes proliferation of gastric cancer cells |
| SMD3 - Small nuclear ribonucleoprotein Sm D3 | 9.0<br>$1.4 \times 10^{-6}$ | Core component of the spliceosome (Cytosol, Nucleus) | Associated with metastatic behavior in soft tissue tumors |
| ITB2 - Integrin beta-2 | 5.9<br>$1.5 \times 10^{-6}$ | Cell adhesion (Plasma membrane, Exosome) | Over-expressed in CLL patients harboring trisomy 12 |
| COPB1 - Coatomer subunit beta 1 | 6.5<br>$1.5 \times 10^{-6}$ | Involved in protein transport from the ER to the Golgi (Cytosol, Golgi) | Over-expressed in prostate cancer |
| MYH9 - myosin 9 | 6.5<br>$1.7 \times 10^{-6}$ | Motor protein (Cytosol) | Highly expressed in CL16 breast cancer cell tumors in mice |
| PSME3 - Proteasome activator complex subunit 3 | >1000<br>$2.6 \times 10^{-6}$ | Subunit of the 11S REG proteasome regulator (Cytosol, Nucleus) | Serum tumor marker for colorectal cancer |
| TM953 - Transmembrane 9 superfamily member 3 | 11.3<br>$2.6 \times 10^{-6}$ | Belongs to nonaspanin protein family. Function not known (Plasma membrane, Golgi) | Diagnostic and therapeutic target for scirrhous-type gastric cancer. Breast cancer chemoresistance factor. |

TABLE 2-continued

NSCLC biomarkers

| Protein name (Uniprot) | Fold change/P value | Proposed function (cell localization) | Relation to cancer |
|---|---|---|---|
| ARPC3 - Actin-related protein 2/3 complex subunit 3 | 8.6<br>$4.2 \times 10^{-6}$ | Component of the Arp2/3 complex involved in regulation of actin polymerization (Cytosol) | Associated with glioma. |
| R515 - 40S ribosomal protein S15 | 15.9<br>$4.3 \times 10^{-6}$ | Translation, component of the 40S subunit (Cytosol, Nucleus) | R515 mutations are associated with increased cancer risk |
| PRKDC - DNA-dependent protein kinase catalytic subunit | 10.1<br>$4.5 \times 10^{-6}$ | Serine/threonine-protein kinase that acts as a molecular sensor for DNA damage (Nucleus) | Highly expressed in advanced neuroblastoma, associated with gastric carcinoma |
| RPN2 - Ribophorin II | 8.8<br>$4.5 \times 10^{-6}$ | Protein glycosylation. Essential subunit of the N-oligosaccharyl transferase (OST) complex (ER Plasma membrane) | Breast cancer initiation and metastasis, associated with docetaxel response in oesophageal SCC |

The identification of cancer biomarkers is a rapidly expanding field, with deep sequencing methods have become widely accepted as a means to detect and analyze cancer biomarkers. At the same time, other cancer-associated changes are not simply reflected as mutations in a gene but rather as increased or decreased expression or variations in post-translational modifications of marker proteins, as reported in some cancers. The present invention identified alterations in the expression levels of metabolic, apoptotic and other proteins in NSCLC as potential means for high sensitive platform that may allow better diagnosis of NSCLC and even early NSCLC diagnosis. Most importantly, the present invention now discloses proteins that allow for distinguishing between the AC and SCC subtypes, which is critical for accurate diagnosis and selection of treatment, particularly in unclear cases.

Over-Expression of Metabolism-Related Proteins in NSCLC—Potential Biomarkers

Figure 4A:
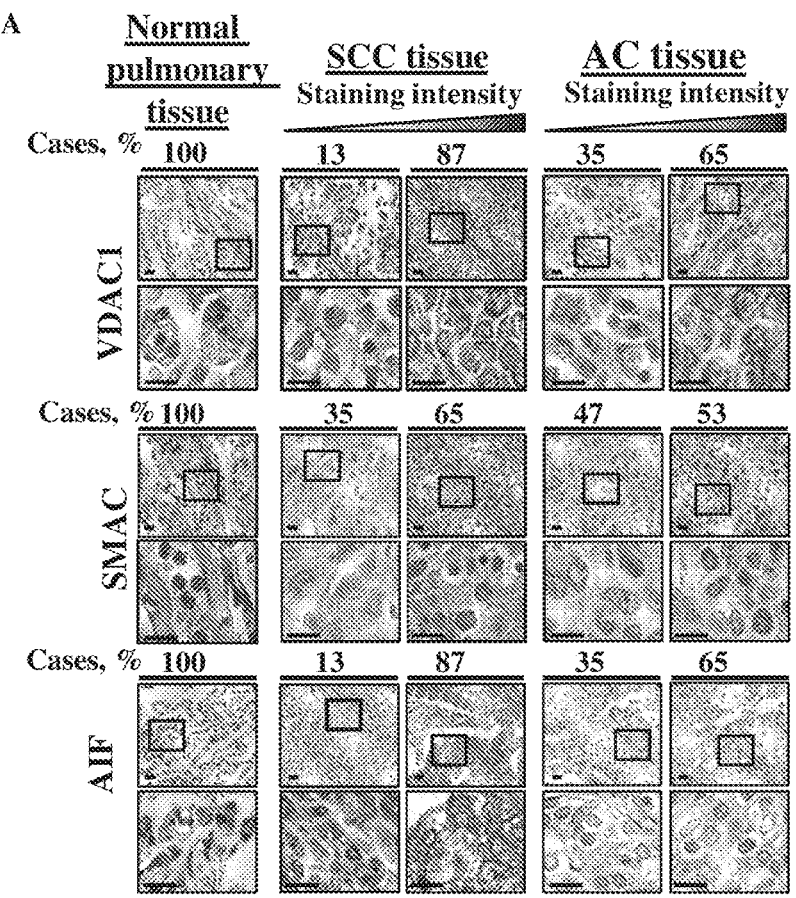
FIG. 4A: IHC staining for VDAC1, AIF and SMAC of human normal lung tissue (n=10), lung SCC tissue (n=31) or lung AC tissue (n=17) in tissue array slides (Biomax), as described in material and methods. Percentages of sections stained at the intensity indicated are shown.
Figure 5A:
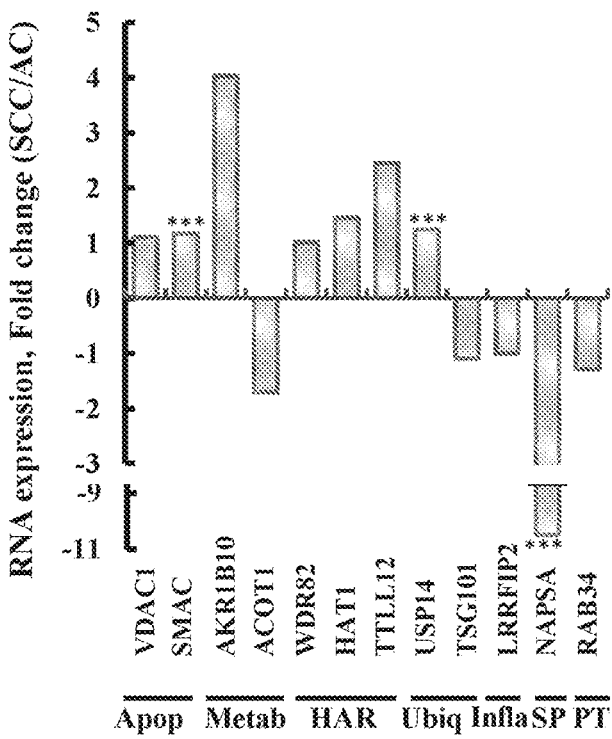
FIG. 5A: RNAseq data imported from TCGA were subjected to quantitative analysis using t-test. The ratio of the expression of the proteins in SCC compared to AC is presented, and is considered statistically significant when $P<0.001$ (***). The proteins were grouped according to function as: Apop, apoptosis; Metab, metabolism; HAR, histone activity regulation; Ubiq, ubiquitination; Inflam, Inflammatory response; SP, Surfactant production; PT, protein transport.

The inventors of the present invention have previously shown that the level of the mitochondrial gatekeeper protein, VDAC1, was substantially higher in different cancer types, in comparison to healthy tissue (WO 2013/035095). As such, its over-expression in NSCLC was also examined (FIG. 2, FIGS. 4A and B and FIG. 5A). Previously, the VDAC1 gene expression level was reported to be increased in NSCLC, with this being associated with poor outcome. As the main transporter of ions, $Ca^{2+}$, ATP, and other metabolites across the outer mitochondrial membrane, VDAC1 over-expression could offer numerous advantages to highly energy-demanding cancer cells. Indeed, the requirement of VDAC1 for cancer development was demonstrated by silencing VDAC1 expression in cancer cells using specific siRNA, resulting in marked inhibition of cancer cells proliferation both in vitro and in vivo.

Figure 3A:
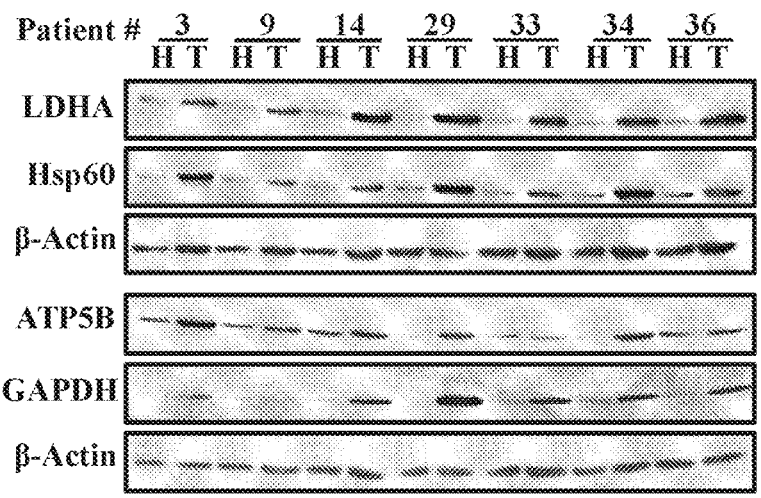
FIG. 3A, B: representative immunoblots of tissue lysates of tumor (T) and healthy (H) lung tissues derived from lung cancer patients probed with antibodies directed against HYOU1 (ORP150), LDHA, HSPD1 (Hsp60), ATP5B, GAPDH and Rab11b.
Figure 3B:
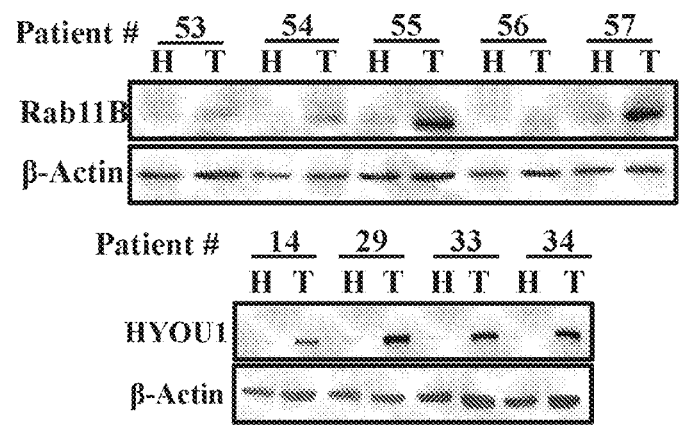
FIG. 3 shows over-expression of known and newly identified proteins in samples obtained from lung cancer patients.
FIG. 3C: quantitative analysis of LC-HR MS/MS data. A difference between healthy and tumor tissues was considered statistically significant when $P<0.001$ (*), $P<0.01$ (), as determined by two-way t-test for the LC-HR MS/MS data.
FIG. 3D: quantitative analysis of gene expression based on RNAseq of GAPDH, PGK1, ENO1, LDHA and HYOU1. The gene expression profiles obtained from healthy (n=110) and tumor lung samples (n=1,017) of lung cancer patients.
Figure 3C:
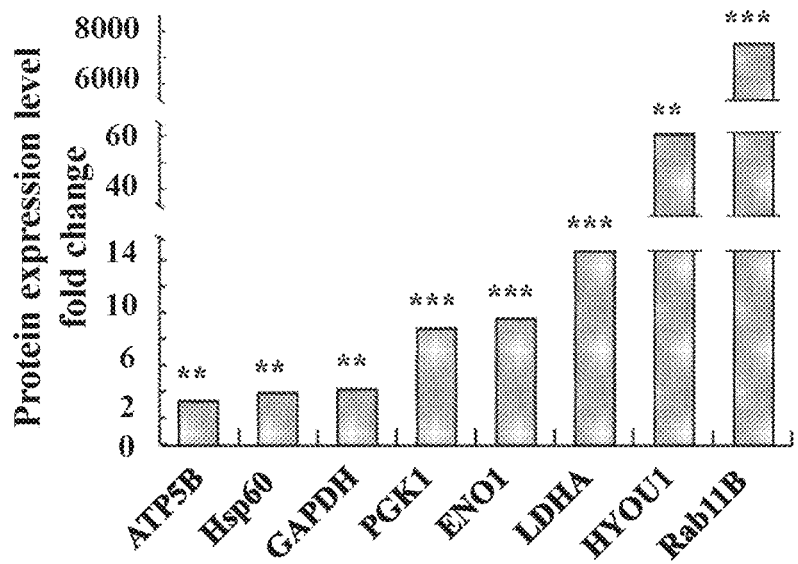
Figure 3D:
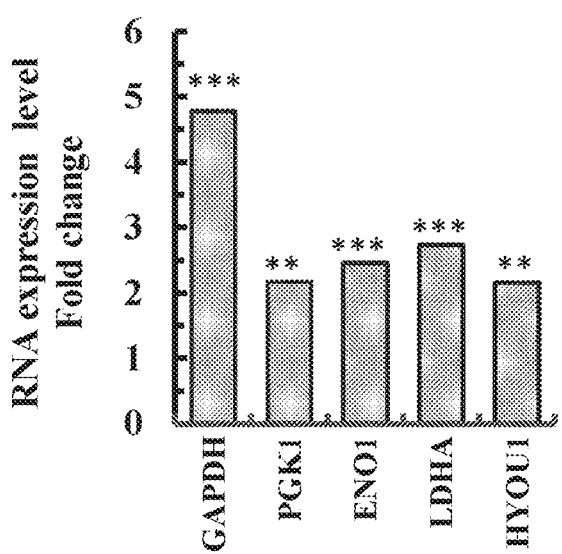

Other metabolism-related proteins that were also shown here to be over-expressed in NSCLC include the glycolytic enzymes PGK1, LDHA, GAPDH, ENO1 and the oxidation phosphorylation (OXPHOS) protein ATP5B (FIG. 3C, Table 6). Of those, PGK1 is shown herein to be associated with NSCLC. Mitochondrial translocated PGK1 functions as a protein kinase, coordinating glycolysis and the TC cycle in tumorigenesis, and acting in tumor angiogenesis as disulphide reductase. PGK1 is activated by both hypoxia and EGFR signaling and was previously found to play a role in brain tumorigenicity (Li X, et al. Mol Cell 2016; 61:705-19) and tumor angiogenesis (Lay A J, et al., Nature. 2000; 408: 869-73). LDHA is over-expressed in several cancer types, including NSCLC (Miao P, et al. IUBMB Life. 2013; 65: 904-10). GAPDH and ENO1 expression or polymorphism is associated with poor prognosis in NSCLC (Puzone R, et al. Mol Cancer. 2013; 12: 97; Lee S Y, et al. Sci Rep. 2016; 6: 35603). Finally, ATP5B, a constituent of the $F_1F_0$ ATP synthase, was identified as NSCLC tumor cellular membrane antigen (Lu Z J, et al., BMC Cancer 2009; 9:16).

Interestingly, network analysis demonstrated that most of these proteins are connected by direct physical interactions or co-expression and some are encoded by a gene cluster that is regulated by epigenetic modifications. Most pronounced is the group of proteins associated with cell metabolic processes. Furthermore, this cluster includes ATP5B associated with OXPHOS and VDAC1, a gatekeeper of mitochondria, suggesting a coupling between OXPHOS and glycolysis, an important factor in cancer cells energy homeostasis (Warburg effect).

These results point to the significance of reprogrammed metabolism in NSCLC, as in other cancers and that the listed proteins may serve as biomarkers.

Expression of the Pro-Apoptotic Proteins SMAC/Diablo and AIF in NSCLC

SMAC/Diablo (second mitochondria-derived activator of caspases, also refered o herein as "SMAC") and AIF (apoptosis inducing factor) are normally located at the mitochondrial intermembrane space and released to the cytosol upon apoptotic signal (Kroemer G, et al. Physiol Rev 2007; 87:99-163). Unexpectedly, despite their pro-apoptotic function, SMAC and AIF were found to be over-expressed in NSCLC, as compared to healthy lung tissue (FIG. 2, FIG. 4 and FIG. 6). SMAC, as a pro-apoptotic protein, is released from mitochondria during apoptosis and counters the inhibitory activities of inhibitor of apoptosis proteins (IAPs) thus releasing their bound caspases. SMAC was found to be over-expressed in some carcinomas and sarcomas, yet showed reduced expression levels in other cancers. This discrepancy between the increased SMAC expression level seen in many cancers and its pro-apoptotic activity may result from another unidentified function of SMAC (Paul, A et al. Mol. Therapy 2018; 26(3):680-694).

AIF is also over-expressed in NSCLC (FIG. 2). AIF, released to the cytosol upon apoptosis induction, translocates to the nucleus, where it triggers chromatin condensation and DNA degradation. As a pro-apoptotic protein, it is not clear why AIF is over-expressed in cancer cells. AIF, however, has emerged as a protein critical for cell survival, as homozygous AIF knockout in mice is embryonically lethal. The pro-survival activity of AIF was proposed to be related to oxidative phosphorylation, ROS detoxification, redox-sensing, mitochondrial morphology and cell cycle regulation. Thus, AIF over-expression in some cancers may offer an advantage to cancer cells via these additional functions.

Unexpectedly, the present invention demonstrates the cellular localization of SMAC/Diablo, being found not only in mitochondria but also in the nucleus, specifically in the nuclei of SCC samples (FIG. 6). Thus, the presence of SMAC/Diablo in the nucleus may be a clear signature for SCC.

Proteins with Modified Expression in NSCLC as Potential Biomarkers

Proteomics (LC-HR MS/MS) analysis of healthy and NSCLC tissues from the same lung revealed several proteins that were highly expressed in the cancer, some of which were previously reported to be associated with other cancers and others are reported as such for the first time here (FIG. 1, FIG. 3, Table 6). These proteins cover a spectrum of functional categories, such as tumor suppressors, protease inhibitors, structural proteins, RNA-binding factors, signaling of immune receptors, coordinators of mitochondrial peptide transmembrane transport, lipid or galactose metabolism or act as protein kinases.

Rab11b protein was over-expressed (~8000-fold) in the tumor tissues, yet was almost absent in the healthy lung tissues in all tested samples (FIG. 3, Table 6). The Rab11 family (Rab11a, Rab11b and Rab25) is associated with recycling endosomes, and Rab25 was previously reported as associated with cancer (Cheng K W, et al. Nat Med 2004; 10:1251-6). Vesicular trafficking in cancer has been suggested to regulate tumor invasion (Steffan J J, et al. PLoS One 2014; 9:e87882).

HYOU1, also known as HSP12A, GRP170 or ORP150, is over-expressed (~60-fold) in lung cancer tissue (FIG. 3, Table 6). HYOU1 is proposed to play an important role in protein folding and secretion in the ER, and contributes to cytoprotection in hypoxia-induced cellular perturbation (Ozawa K, et al. J Biol Chem 1999; 274:6397-404). HYOU1 was shown to be up-regulated in breast and nasopharyngeal carcinomas, and was associated with tumor invasiveness and poor prognosis. It was also shown to be overexpressed in NSCLC (BC, Rom W, et al. Clin Proteomics. 2016; 13: 31).

EGFR and MEK1 were found to be over-expressed in the tumor, as compared to healthy lung tissues (Table 6). Hyperactivation of the EGFR-Ras-MAPK pathway, with the involvement of mutated protein versions, is the most common alteration in lung cancer (Campbell et al. 2016, ibid; Paez J G, et al. Science 2004; 304:1497-500; Mitsudomi T, et al. Cancer Sci 2007; 98:1817-24). Thus many of these proteins may serve as NSCLC biomarkers.

Biomarkers for SCC and AC Diagnosis

The two main subtypes of NSCLC, AC and SCC, show differences in mutation within the genome, epigenome, transcriptome, and proteome (Campbell et al., 2016, ibid). Thyroid transcription factor-1 (TTF-1) is currently used in the clinic to distinguish between AC and SCC (Fujita J, et al. Lung Cancer 2003; 39:31-6). Nevertheless, it is still challenging distinguishing between these two NSCLC sub-types (Zakowski M F, et al. Arch Pathol Lab Med 2016; 140:1116-20). Precise diagnosis is essential for selecting the appropriate treatment and thus increasing a patient's life expectancy.

The present invention discloses newly identified proteins that allow for distinguishing between AC and SCC and also confirm the differential expression of several previously reported proteins (Tables 7 and 10). Compared to samples from healthy tissues, the expression of HAT1, LRRFIP2, AKR1B10, WDR82, TTLL12, IGF2BP3, and SMC2 was demonstrated to be upregulated in NSCLC subtype SCC and downregulated in NSCLC subtype AC. The expression level of ACAD8, RSU1, ACOT1, HYOU1 and GALE was upregulated in NSCLC subtype AC while it was downregulated in NSCLC subtype SCC. The expression level of ITGA7 was upregulated in both SCC and AC subtypes, but with a significantly more pronounced upregulation in SCC. Same pattern was shown for USP14, known to be overexpressed in NSCLC. On the other hand, the expression of TSG10, while also upregulated in both subtype, was significantly higher in AC compared to SCC. The expression level of RAB34 was downregulated compared to the healthy control in both AC and SCC, but the reduction was significantly lower in AC compared to SCC.

Figure 4B:
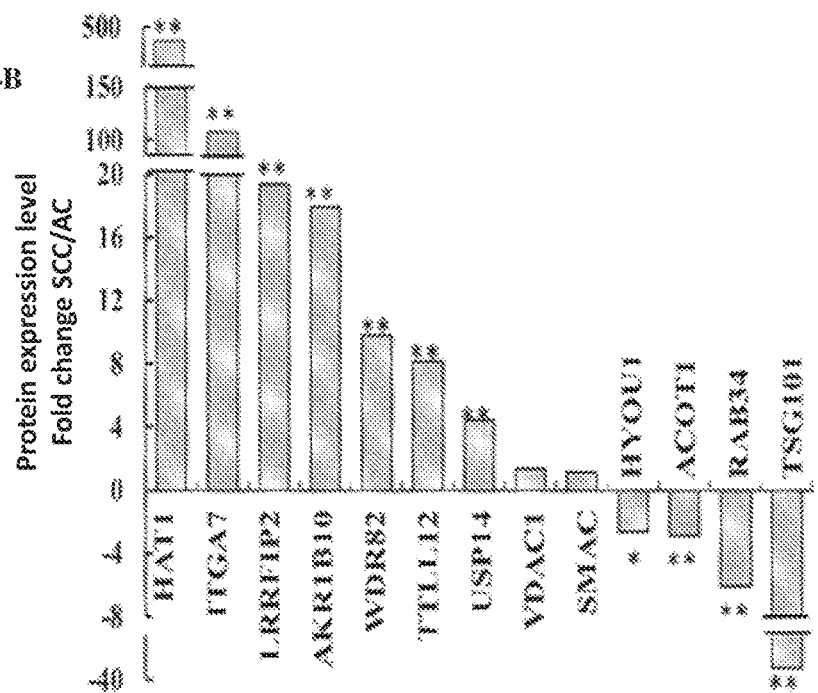
FIG. 4B: LC-HR MS/MS data were used to identify proteins that can serve to distinguish between AC and SCC. A difference between AC and SCC groups was considered statistically significant when $P<0.05$ (*), $P<0.01$ () or $P<0.001$ (*) as determined by the Mann-Whitney test.

AKR1B10 has been previously reported as a potential diagnostic marker specific to smokers' NSCLCs; TSG101 was shown to be involved in lung cancer cell proliferation and IGF2BP3 was reported to be over-expressed in various types of cancer, including NSCLC. Several of the proteins have been proposed to be associated with cancer, but not with NSCLC. TTL12 and HAT1 were previously reported to be associated with prostate cancer or lymphoma and esophageal squamous cell carcinoma progression, respectively (Table 7). ITGA7 has been shown to be associated with the occurrence and development of bladder cancer. RAB34 has been reported as a progression- and prognosis-associated biomarker in gliomas and Ras-associated sarcomagenesis. LRRFIP2, WDR82, ACOT1, SMC2, ACAD8, GALE, and RSU1 were not identified previously as possible biomarkers for any type of cancer (FIG. 4B, Table 7). Finally, the expression levels of several of these proteins affected AC patient survival but had no effect on SCC survival (Table 9).

Figure 5B:
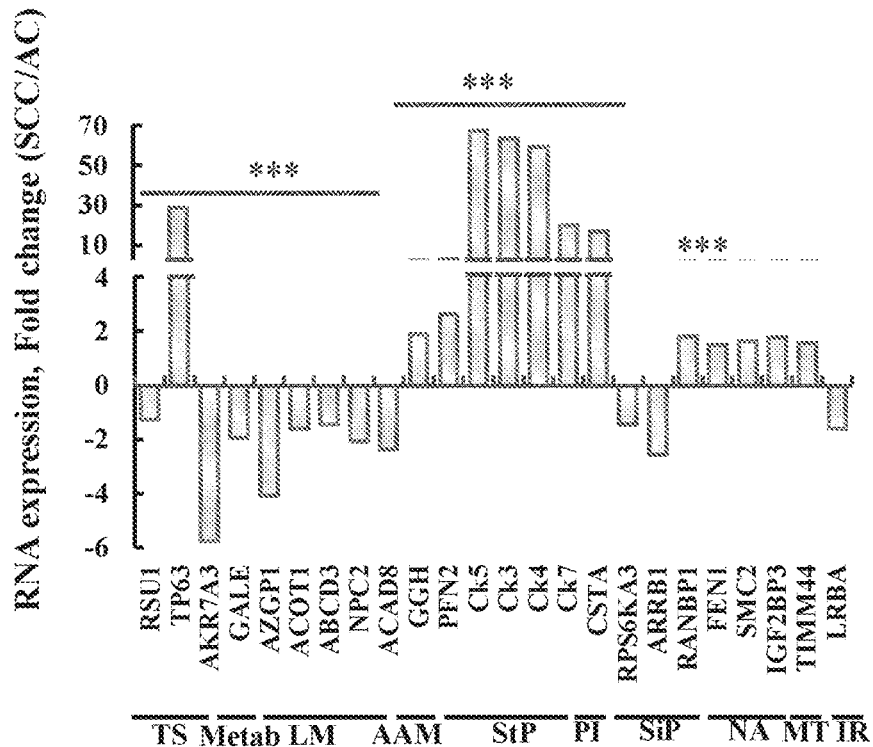
FIG. 5B: Quantitative analysis of RNAseq data of 24 selected genes showing differential expression between AC and SCC based on proteomics data, Functional groups are indicated: TS, tumor suppressor; Metab, galactose metabolism); LM, lipid metabolism; AAM, amino acid metabolism; StP, structural proteins; PI, proteinase inhibitor; SiP, signaling pathway; NA, nuclear activity; MT, mitochondrial translocase and IR, immune response.

As demonstrated herein, proteins selected based on their differential expression levels in AC and SCC as revealed by LC-HR MS/MS (FIG. 4B) typically showed differential RNA levels in SCC and AC (FIG. 5A). Further analysis of RNAseq UCSC XENA data, selecting genes encoding proteins showing differential expression levels in AC and SCC (LC-HR MS/MS data) was performed. The mRNA levels encoding for proteins associated with variety of functions were changed in AC and SCC (3-60-fold) (FIG. 5B). This analysis confirmed previous reports suggesting TP63 and Ck5, Ck13, Ck14, Ck17, CSTA and PFN2 as biomarkers for SCC. AKR7A3 and ACAD8 were identified here for the first time as being over-expressed in AC (2-6-fold), relative to their expression levels in SCC (FIG. 5B). Genes such as NPC2 (Niemann-Pick disease, type C2), a secreted protein, and ARRB1, were previously reported as biomarkers for lung AC and confirmed here (Tables 8 and 10).

Another interesting group of genes that are highly expressed in AC, relative to SCC, are those associated with fatty acid/lipid metabolism and transport. Previously reported to be associated with AC is AZGP1 (zinc-alpha2-glycoprotein) (Albertus D L, et al. J Thorac Oncol 2008; 3:1236-44), a secreted protein that stimulates lipid degradation in adipocytes and causes the extensive fat losses associated with some advanced cancers (Bing C, et al. Proc Natl Acad Sci USA 2004; 101:2500-5). ACOT1 (acyl-CoA thioesterase 1) a secreted protein that is a regulator of peroxisomal lipid metabolism (Hunt M C, et al. J Biol Chem 2002; 277:1128-38), and ACAD8 (isobutyryl-CoA dehydrogenase), a mitochondrial protein catalyzing the dehydrogenation of acyl-CoA derivatives in the metabolism of fatty acids or branched-chain amino acids such as valine (Battaile K P, et al. J Biol Chem 2004; 279:16526-34), are reported herein as markers for NSCLC subtype AC for the first time. In this respect, AC mostly originates from alveolar type 2 (AT2) cells, with lipid metabolism systems being part of surfactant production associated with these cells.

Collectively, based on the expression levels (fold change), specific expression in AC or SCC of protein/mRNA identified here for the first time, or in previous reports and confirmed here, we propose a list of proteins differentially expressed in SCC and AC, of which four are secreted proteins (Tables 7, 8 and 10) that can be used to clearly distinguish between SCC or AC. This is of high importance for guiding the appropriate treatment for these two NSCLC sub-types. In summary, the present invention identified several proteins the expression levels of which are highly increased in lung cancer patients. Moreover, some of these biomarkers can be used as profiling platforms enable to distinguish between AC and SCC. The use of these molecules may facilitate accurate diagnosis and prognostic prediction and could contribute to individualized lung cancer treatment. Finally, the search for drugs that target the biomarkers differentially expressed in NSCLC subtype AC and NSCLC subtype SCC may lead to new specific treatments for each of the lung cancer subtypes.

Methods of Measuring Expression Level

Comparing an expression level of a biomarker of the invention to its expression in a control sample or to a reference value comprises measuring and determining the expression level of the biomarker in a biological sample. Any method for detecting the marker expression as is known to a person skilled in the art may be used according to the teachings of the present invention. In some embodiments, the expression level can be measured by proteomic analysis methods as known in the art. Proteomics is the practice of identifying and quantifying the proteins, or the ratios of the amounts of proteins expressed in cells and tissues.

Those skilled in the art will be familiar with numerous specific immunoassay formats and variations thereof which may be useful for carrying out the method disclosed herein including enzyme linked immunosorbent assays (ELISAs), enzyme linked immunospot assay (ELISPOT), LC-HR MS/MS analysis, radioimmunoassays (RIA), radioimmune precipitation assays (RIPA), immunobead capture assays, Western blotting, dot blotting, gel-shift assays, flow cytometry, immunohistochemistry (IHC), fluorescence microscopy, protein arrays, multiplexed bead arrays, magnetic capture, and in vivo imaging. See generally E. Maggio, Enzyme-Immunoassay, (1980) (CRC Press, Inc., Boca Raton, Fla.).

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to lung-specific protein from specific species such as rat, mouse, or human can be selected to obtain only those polyclonal antibodies that are specifically immunoreactive with lung-specific protein and not with other proteins, except for polymorphic variants and alleles of the lung specific protein. This selection may be achieved by subtracting out antibodies that cross-react with lung-specific protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically, a specific or selective reaction will be at least twice the background signal or noise and more typically more than 10 to 100 times the background signal.

In some embodiments, the level of the biomarker is measured by contacting the biological sample with a specific antibody. A specific antibody may be for example a polyclonal antibody, a monoclonal antibody, a chimeric antibody, a human antibody, an affinity maturated antibody or an antibody fragment. While monoclonal antibodies are highly specific to a marker/antigen, a polyclonal antibody can preferably be used as a capture antibody to immobilize as much of the marker/antigen as possible.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen. If desired, the marker may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal. The antibodies are then obtained from blood samples taken from the animal. The techniques used to produce polyclonal antibodies are extensively described in the literature (see, e.g., Methods of Enzymology, "Production of Antisera with Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies.

Monoclonal antibodies (mAbs) may be readily prepared through use of well-known techniques, such as those exemplified in U.S. Pat. No. 4,196,265. Typically, this technique involves immunizing a suitable animal with a selected immunogen composition, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages but mice are preferred, with the BALB/c mouse being most preferred as this is most routinely used and generally gives a higher percentage of stable fusions.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 1251, 1311), enzyme labels (e.g., horseradish peroxidase, alkaline phosphatase), and fluorescent labels (e.g., fluorescein, Alexa, green fluorescent protein, rhodamine) in accordance with known techniques.

Immunohistochemical staining may also be used to measure the differential expression of a biomarker or a plurality of biomarkers. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme as described hereinabove. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker. According to certain embodiments, the biomarker expression is measured by IHC.

According to some embodiments, the level of the biomarker is measured by proteomic analysis. According to certain embodiments, the biomarker expression is measured by LC-MS/MS.

Nucleic Acid Testing (NAT) Assays

According to some embodiments, the methods of the invention comprise the comparing and/or detecting the expression level of genes.

Detection of a nucleic acid of interest in a biological sample may be effected by NAT-based assays, which involve nucleic acid amplification technology, such as PCR or variations thereof e.g. real-time PCR, quantitative PCR (qPCR) and the like.

Amplification of a selected or target nucleic acid sequence may be carried out by a number of suitable methods. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and Nucleic acid sequence-based amplification (NASBA).

Quantitative real-time PCR (QRT-PCR) may be used to measure the differential expression of a marker or a plurality of biomarkers. In QRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified. A non-limiting example of a fluorescent reporter probe is a TaqMan™ probe (Applied Biosystems, Foster City, Calif.). The fluorescent reporter probe fluoresces when the quencher is removed during the PCR extension cycle. Muliplex QRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, QRT-PCR is typically performed using a reference standard. The ideal reference standard is expressed at a constant level among different tissues, and is unaffected by the experimental treatment. Suitable reference standards include, but are not limited to, mRNAs for the housekeeping genes glyceraldehyde-3-phosphate-dehydrogenase (GAPDH) and beta-actin. The level of mRNA in the original sample or the fold change in expression of each biomarker may be determined using calculations well known in the art.

A nucleic acid microarray may be used to quantify the differential expression of a plurality of biomarkers. Microarray analysis may be performed using commercially available equipment, following manufacturer's protocols. Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

Kits

In some embodiments, the present invention provides an article of manufacture e.g., kit, such as an FDA approved kit, which contains diagnostic or prognosis reagents and instructions for use. The kit, in some embodiments, is accommodated by a notice associated with the container in a form prescribed by a regulatory agency regarding the manufacture, use or sale of pharmaceuticals, which notice is reflective of approval by the agency of the form of the compositions or human use.

According to certain aspects, the present invention provides a kit for diagnosing a subtype of non-small cell lung carcinoma (NSCLC) selected from adenocarcinoma (AC) and squamous cell carcinoma (SCC) in a biological sample obtained from a subject suspected to have NSCLC, the kit comprising:

(a) at least one agent capable of detecting the expression level of at least biomarker selected from a protein and mRNA encoding the protein, the biomarker is selected from the group consisting of HAT1, LRRFIP2, AKR1B10, WDR82, TTL12, IGF2BP3, SMC2, ACAD8, RSU1, ACOT1, HYOU1, GALE, ITGA7, TSG101, and RAB34;

(b) means for comparing the expression level of the at least one biomarker to a first reference value derived from the expression of the at least one biomarker in healthy biological sample and/or to a second reference value derived from the fold change of the expression of said at least one biomarker in a plurality of samples obtained from SCC patients compared to the expression in a plurality of healthy biological samples; and/or to a third reference value derived from a fold change of the expression of the at least one biomarker in a plurality of samples obtained from AC patients compared to a plurality of healthy biological samples;

(c) instruction material providing guidance to the correlation of said expression level of said at least one biomarker with the NSCLC subtype, wherein:

an increased expression level in said sample of at least one biomarker selected from the group consisting of HAT1, LRRFIP2, AKR1B10, WDR82, TTL12, IGF2BP3, and SMC2, and/or reduced expression of at least one biomarker selected from the group consisting of ACAD8, RSU1, ACOT1, HYOU1, and GALE compared to the first reference value indicates that said subject has NSCLC subtype SCC;

a reduced expression level in the sample of at least one biomarker selected from the group consisting of HAT1, LRRFIP2, AKR1B10, WDR82, TTL12, IGF2BP3, and SMC2, and/or elevated expression of at least one biomarker selected from the group consisting of ACAD8, RSU1, ACOT1, HYOU1, and GALE compared to the first reference value indicates that said subject has NSCLC subtype AC;

an equal or elevated fold change of the biomarker TGA7 compared to the second reference value indicates that the subject has NSCLC subtype SCC;

an equal or elevated fold change of the biomarker TSG101 compared to the third reference value indicates that the subject has NSCLC subtype AC; and/or an equal or reduced fold change of the biomarker RAB34 compared to the third reference value indicates that the subject has NSCLC subtype AC.

According to certain embodiments, the kit further comprises at least one agent capable of detecting the expression of SMAC/Diablo protein within the nucleus of cells present within the biological sample and instruction material providing guidance to correlation of the amount of SMAC/Diablo within the cell nucleus and the cytosol and NSCLC subtype, wherein a significant amount of the SMAC/Diablo protein in the cell nucleus and cytosol diagnose the subject as having NSCLC subtype SCC and no significant amount of said SMAC/Diablo protein in the cell nucleus while a significant amount is present in the cytosol diagnose the subject as having NSCLC subtype AC.

According to certain additional aspects, the present invention provides a kit for diagnosing NSCLC, the kit comprising:

(a) at least one agent capable of detecting the expression level of at least one biomarker selected from a protein and mRNA encoding said protein, the biomarker is selected from the group consisting of APOOL, VPS29, and CAF17 in a biological sample of a subject suspected of having NSCLC;

(b) means for comparing the expression level of the at least one biomarker in a control sample obtained from a healthy subject or to a reference value; and (c) instruction material providing guidance to the correlation of an increase in the expression level of said at least one biomarker compared to the control sample or to the reference value with NSCLC.

The kits may include antibodies, protein arrays, reagents for use in immunoassays, protein controls, RNA arrays, reagents for use in NAT-based assays, instruction sheets in addition to the guidance instruction material, gene expression database, and/or any means for determining and analyzing the expression level of the protein or RNA biomarkers according to the teachings of the invention.

Method of Treating NSCLC, NSCLC Subtype AC and NSCLC Sybtype AC

The diagnostic methods of the present invention may further comprise treating the subject according to the diagnosis, and the present invention further provides method of treating a subject having NSCLC, NSCLC subtype AC or NSCLC subtype SCC. The principle underlying these methods is administering the subject and agent reducing the expression or activity of proteins highly expressed in each of these diseases.

According to certain aspects, the present invention provides an agent reducing the expression or activity of at least one protein selected from the group consisting of HAT1, LRRFIP2, AKR1B10, WDR82, TTLL12, ITGA7, IGF2BP3, and USP14 for use in treating NSCLC subtype SCC.

According to certain additional aspects, the present invention provides an agent reducing the expression or activity of at least one protein selected from the group consisting of ACAD8, TSG101, and GALE for use in treating NSCLC subtype AC.

According to yet further aspects, the present invention provides an agent reducing the expression or activity of at least one protein selected from the group consisting of APOOL, VPS29, and CAF17 for use in treating NSCLC.

According to some embodiments, the agent reducing the expression or activity of the at least one protein is selected from the group consisting of a chemical agent or moiety, a protein, a peptide, and a polynucleotide molecule.

According to some embodiments, the agent is an antibody. Methods for preparing antibodies specifically binding to the protein of interest are known in the art and described hereinabove.

According to some embodiments, the agent is an interfering RNA (RNAi) molecule. In certain embodiments, the interfering RNA molecule is selected from the group consisting of a shRNA, a siRNA, and a miRNA.

In certain aspects, an interfering RNA of the invention has a length of about 19 to about 49 nucleotides. In other aspects, the interfering RNA comprises a sense nucleotide strand and an antisense nucleotide strand.

RNA interference (RNAi) is a process by which double-stranded RNA (dsRNA) is used to silence gene expression. While not wishing to be bound by any theory or mechanism of action, RNAi begins with the cleavage of longer dsRNAs into small interfering RNAs (siRNAs) by an RNaseIII-like enzyme, dicer. SiRNAs are dsRNAs that are typically about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA.

Those of skill in the art will recognize that, in principle, either strand of siRNA molecule can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Pharmaceutical Compositions

The agents of the present invention can be administered to a subject per se, or in a pharmaceutical composition where they are mixed with suitable carriers or excipients. Examples of suitable pharmaceutically acceptable carriers may include water, saline, PBS (phosphate buffered saline), dextrin, glycerol, and ethanol. The pharmaceutically acceptable carrier may be formulated for administration to a human subject or patient. The composition may be formulated into a dosage form which can release the active ingredient in a rapid or a sustained or delayed manner after administration.

According to some embodiments, the composition comprises as an active agent an interfering RNA molecule.

The interfering RNA molecule can be administered in a variety of methods as known in the art. Systemically administered RNA is rapidly cleared by the kidneys or liver due to its high solubility in water and negative charge. Therefore, according to some embodiments, the RNA is encapsulated. The encapsulation might enhance the circulation time of the RNA in the body and prevent degradation by extracellular nucleases. According to some embodiments, the pharmaceutical composition comprises a siRNA component and lipid component. According to certain embodiments, the interfering RNA molecule is administered within liposome. For example, WO2006113679 provides methods for the delivery of RNA interfering molecules to a cell via a neutral (non-charged) liposome. WO201011317 describes the use of amphoteric liposomal compositions for cellular delivery of small RNA molecules for use in RNA interference.

According to other embodiments, the interfering RNA molecule is administered directly or via a nucleic acid delivery system. The system may comprise a compound that stabilizes the RNA, such as a lipid or a protein. For example, WO1995022618 discloses a delivery system that contains a fusion protein having a target moiety and a nucleic acid binding moiety.

According to other embodiments, the composition comprises as an active agent at least one antibody specific to one biomarker according to the teachings of the invention.

The actual dosage amount of a composition of the present invention administered to a patient or subject can be determined by physical and physiological factors such as body weight, severity of condition, previous or concurrent therapeutic interventions, and on the route of administration. The practitioner responsible for administration will determine the concentration of active ingredient(s) in a composition and appropriate dose(s) for the individual subject.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Materials

Phenylmethylsulfonyl fluoride (PMSF), propidium iodide (PI), and trypan blue were purchased from Sigma (St. Louis, Mo.). Dulbecco's modified Eagle's medium (DMEM) and the supplements fetal calf serum, L-glutamine and penicillin-streptomycin were purchased from Biological Industries (Beit Haemek, Israel). Horseradish peroxidase (HRP)-conjugated anti-mouse, anti-rabbit and anti-goat antibodies were from KPL (Gaithersburg, Md.). 3,3-diaminobenzidine (DAB) was obtained from ImmPact-DAB (Burlingame, Calif.). Primary antibodies used in immunoblotting and immunohistochemistry (IHC), as well as their dilutions, are listed in Table 3.

TABLE 3

Antibodies used
Antibodies against the indicated protein, their catalogue number, source and the dilutions used in IHC and immunoblot experiments (Western blots, WB) are presented.

| Antibody | Source and Catalogue Number | Dilution used IHC | Dilution used WB |
|---|---|---|---|
| Mouse monoclonal anti-β-Actin | Millipore, Billerica, MA, MAB1501 | — | 1:10,000 |
| Mouse monoclonal anti-ATP5B | Abcam, Cambridge, UK, ab14730 | — | 1:10,000 |
| Rabbit monoclonal anti-AIF | Abcam, ab32516 | 1:200 | 1:1000 |
| Mouse monoclonal anti-Bcl-2 | Calbiochem, Nottingham UK, OP60 | — | 1:2000 |
| Mouse monoclonal anti-HK-I | Abcam, ab105213 | 1:500 | 1:2000 |
| Rabbit monoclonal anti-HK II | Santa Cruz Biotechnology Dallas, TX, sc-27230 | — | 1:1000 |
| Goat polyclonal anti-LDHA | Epitomics, Cambridge, UK, 1980-1 | 1:300 | 1:1000 |
| Rabbit polyclonal anti-MAVS | ALX-210-929-C100 | | 1:2000 |
| Rabbit monoclonal anti-HYOU1 | Abcam, ab134944 | | 1:3000 |
| Rabbit monoclonal anti-Hsp60 | Abcam, ab46798 | — | 1:10,000 |
| Mouse monoclonal anti-GAPDH | Abcam, ab9484 | — | 1:1000 |
| Rabbit monoclonal anti-Rab11b | Santa Cruz Biotechnology, Dallas, TX, ab3612 | — | 1:1000 |
| Rabbit monoclona lanti-SMAC/Diablo | Abcam, ab8115 | 1:300 | 1:2000 |
| Rabbit monoclonal anti-VDAC1 | Abcam, ab15895 | 1:500 | 1:5000 |
| Goat anti-Rabbit-HRP | KPL, Gaithersburg, PA, 474-1506 | 1:250 | 1:15,000 |
| Donkey anti-Goat-HRP | Abcam, ab97120 | — | 1:20,000 |

Patients

All the investigations presented in this study were conducted after informed consent was obtained and in accordance with an institutional review board protocol approved by the Ethics Committee of Soroka University Medical Center. All human tissues were collected with the understanding and written consent of each subject, and the study methodologies conformed to the standards set by the Declaration of Helsinki.

NSCLC specimens were obtained from 2010 to 2016 from 46 patients who underwent lung resection without any treatment at the time of surgery. The main clinical and pathologic variables of the patients are provided in Table 4.

Fresh paired healthy and cancer tissue specimens were obtained from the same lung cancer patient who underwent either pneumonectomy or pulmonary lobectomy to remove tumors tissue. The specimens were immediately frozen in liquid nitrogen and maintained at −80° C. until analysis by immunoblotting or qPCR. Proteins were extracted from the tissue sample as described below. Cancer and normal lung tissue surrounding the tumor were validated by hospital pathologists.

Twenty-eight patients were males and twenty-seven were females, with an average age of 68 years (range, 36-86). Disease stage was staged according to the international tumor-node-metastasis system (TMM) and then classified to the ranging from occult cancer, through stage 0, IA, IB, IIA, IIB, IIIA, IIIB to IV (grade I, n=30), (grade II, n=10), (grade III, n=5) (grade IV, n=1).

TABLE 4

Lung cancer patient characteristics

| Patient No. | Age (years) | Gender | Type of Cancer | Stage of Disease |
|---|---|---|---|---|
| 1 | 76 | F | AC | 2B |
| 2 | 77 | M | SCC | 1A |
| 3 | 54 | M | AC | 3A |
| 4 | 58 | M | SCC | 2B |
| 5 | 70 | M | SCC | 2B |
| 6 | 69 | F | AC | 2A |
| 7 | 36 | M | AC | 3A |
| 8 | 62 | M | AC | 1A |
| 9 | 82 | M | AC | 2A |
| 10 | 48 | M | AC | 1A |
| 11 | 65 | F | AC | 1A |
| 12 | 78 | M | SCC | 1B |
| 13 | 72 | M | AC | 1A |
| 14 | 78 | M | AC | 1A |
| 15 | 55 | M | AC | 1A |
| 16 | 59 | F | SCC | 1A |
| 17 | 74 | F | SCC | 2A |
| 18 | 65 | M | SCC | 4 |
| 19 | 76 | M | SCC | 3A |
| 20 | 65 | F | SCC | 1A |
| 21 | 61 | M | AC | 1A |
| 22 | 54 | M | SCC | 1B |
| 23 | 56 | F | AC | 1A |
| 24 | 58 | M | AC | 1A |
| 25 | 55 | F | AC | 1A |
| 26 | 76 | F | AC | 1A |
| 27 | 85 | M | AC | 1B |
| 28 | 55 | F | AC | 1A |
| 29 | 62 | M | AC | 2A |
| 30 | 79 | M | AC | 3A |
| 31 | 81 | M | AC | 1A |
| 32 | 62 | F | AC | 1B |
| 33 | 83 | F | SCC | 1B |
| 34 | 77 | M | SCC | 1A |
| 35 | 86 | M | SCC | 1B |
| 36 | 74 | M | SCC | 1B |
| 37 | 74 | M | AC | 1A |
| 38 | 67 | F | AC | 2A |
| 39 | 71 | M | AC | 1A |
| 40 | 75 | F | AC | 3A |
| 41 | 85 | M | SCC | 1A |
| 42 | 77 | M | SCC | 2A |
| 43 | 59 | F | SCC | 2A |
| 44 | 59 | F | SCC | 1B |
| 45 | 58 | M | AC | 1B |
| 46 | 68 | F | AC | 1A |

Protein Extraction from Lung Tissue

To extract proteins for immunoblotting, healthy and tumor lung tissues were solubilized in a lysis buffer (50 mM Tris-HCl, pH 7.5, 150 mM NaCl, 1 mM EDTA, 1.5 mM $MgCl_2$, 10% glycerol, 1% Triton X-100, a protease inhibitor cocktail (Calbiochem)), followed by sonication and centrifugation (10 min, 600 g). The protein concentration of each lysate was determined using Lowry assay. Samples were stored in −80° C. until analysis by gel electrophoresis and immunoblotting, as described hereinbelow. To extract proteins for LC-HR MS/MS, healthy and tumor lung tissues were solubilized in a different lysis buffer (100 mM Tris-HCl, pH 8.0, 5 mM DTT, 4% SDS and a protease inhibitor cocktail (Calbiochem; 100 µl/10 mg)), followed by homogenization, incubation for 3 min at 95° C. and centrifugation (10 min, 15,000 g). The protein concentration of each lysate was determined using Lowry assay. Samples were stored in −80° C. until MS/MS analysis, as described hereinbelow.

Gel Electrophoresis and Immunoblotting

Samples (10-40 µg of protein) were subjected to SDS-PAGE. Gels were stained with Coomassie Brilliant Blue or electro-transferred onto nitrocellulose membranes for immunostaining. Membranes containing the transferred proteins were blocked with 5% non-fat dry milk and 0.1% Tween-20 in Tris-buffered saline (TBS) and incubated overnight at 4° C. with the different primary antibodies (sources and dilutions as detailed in Table 3), followed by incubation with the appropriate HRP-conjugated secondary antibodies for 1 h. Enhanced chemiluminescence (Biological Industries) was used for detection of HRP activity. Band intensities were analyzed using FUSION-FX (Vilber Lourmat, France) and the values were normalized to the intensities of the appropriate α-actin signal that served as a loading control.

RNA Isolation and qPCR

Total RNA was isolated from healthy and tumor lung samples using an RNeasy mini kit (Qiagen) according to the manufacturer's instructions. Total RNA quality was analyzed using the Agilent RNA 6000 nano kit. qPCR was performed using specific primers (KiCqStart Primers; Sigma Aldrich) in triplicate, using Power SYBER green master mix (Applied Biosystems, Foster City, Calif.). Levels of target genes were normalized relative to 3-actin mRNA levels. Samples were amplified by a 7300 Real Time PCR System (Applied Biosystems) for 40 cycles using the following PCR parameters: 95° C. for 15 seconds, 60° C. for 1 minute, and 72° C. for 1 minute. The copy numbers for each sample were calculated by the CT-based calibrated standard curve method. The mean fold changes (±SEM) of the three replicates were calculated. Genes examined and primers used are listed in Table 5.

TABLE 5 qPCR primers used in this study

| Gene | Primer sequences | SEQ ID NO |
|---|---|---|
| β-Actin | Forward 5'-ACTCTTCCAGCCTTCCTTCC-3' | 1 |
| | Reverse 5'-TGTTGGCGTACAGGTCTTTG-3' | 2 |
| AKR1B10 | Forward 5'-GAGCAGGACGTGAGACTTCT-3' | 3 |
| | Reverse 5'-TTTGCCAAGAGGAGACTTCCAA-3' | 4 |
| USP14 | Forward 5'-TGCCCTTAAAAGGTATGCAGGT-3' | 5 |
| | Reverse 5'-TCTCGGCAAACTGTGGGAAA-3' | 6 |
| TTLL12 | Forward 5'-TGGAGCACGAGGTTTTCGAC-3' | 7 |
| | Reverse 5'-CGATGACCTTGTAGCACAGC-3' | 8 |
| TSG101 | Forward 5'-GCCAGCTCAAGAAAATGGTGT-3' | 9 |
| | Reverse 5'-AGGTCTCTGTATTTGTACTGGGT-3' | 10 |
| LRRF2 | Forward 5'-CCTCAGCAACAACCCCTCTA-3' | 11 |
| | Reverse 5'-GGTCATAGATATCCCGCAATTCA-3' | 12 |
| WDR82 | Forward 5'-GCTTCGATTTCAGCCCCAAC-3' | 13 |
| | Reverse 5'-TCTCTTTGGTTTGCCCTCCT-3' | 14 |
| HAT1 | Forward 5'-ATGGCGGGATTTGGTGCTAT-3' | 15 |
| | Reverse 5'-GTTCAATTGCTGTGTTGGTGT-3' | 16 |

LC-HR MS/MS Analysis

Samples were subjected to in-solution tryptic digestion as follows: proteins were first reduced by incubation with 5 mM DTT for 30 min at 60° C., followed by alkylation with 10 mM iodoacetamide in the dark for 30 min at 21° ° C. Proteins were then subjected to digestion with trypsin (Promega, Madison, Wis.) at a 1:50 trypsin:protein ratio for 16 h at 37° C. Following digestion, detergents were cleared from the samples using commercial detergent removal columns (Pierce, Rockford, Ill.), and desalted using solid-phase extraction columns (Oasis HLB, Waters, Milford, Mass.). Digestion was stopped by addition of trifluroacetic acid (1%). The samples were stored at −80° C. until LC-HR MS/MS analysis.

For LC-HR MS/MS, ULC/MS grade solvents were used for all chromatographic steps. Each sample was separated using split-less nano-ultra performance liquid chromatography columns (10 kpsi nanoAcquity; Waters). The mobile phase was (A) $H_2O$ and 0.1% formic acid, and (B) acetonitrile and 0.1% formic acid. Desalting of the samples was performed online using a reverse-phase C18 trapping column (180 m internal diameter, 20 mm length, 5 m particle size; Waters). The peptides were then separated using a T3 HSS nano-column (75 m internal diameter, 250 mm length, 1.8 m particle size; Waters) at 0.3 L/min. Peptides were eluted from the column into the mass spectrometer using the following gradient: 4% to 35% (B) for 150 min, 35% to 90% (B) for 5 min, maintained at 90% for 5 min and then back to initial conditions. The nano-UPLC was coupled online through a nano-ESI emitter (10 µm tip; New Objective, Woburn, Mass.) to a quadrupole Orbitrap mass spectrometer (Q Executive, Thermo Scientific) using a Flexlon nanospray apparatus (Proxeon). Data were acquired in the DDA mode, using a Top12 method (Kelstrup C D, et al. J Proteome Res. 2012; 11: 3487-97). Raw data was imported into Expressionist software (Genedata) (Ueda K, et al. PLoS One. 2011; 6:e18567; Guryca V, et al. Proteomics. 2012; 12: 1207-1216). The software was used for retention time alignment and peak detection of precursor peptide intensities. A master peak list was generated from all MS/MS events and sent for database searching using Mascot v2.4 (Matrix Sciences). Data were searched against a database containing forward and reverse human protein sequences from UniprotKB/SwissProt, and 125 common laboratory contaminants, totaling 20,304 entries. Fixed modification was set to carbamidomethylation of cysteines, while variable modification was set to oxidation of methionines. Search results were then imported back to Expressionist for annotation of detected peaks. Identifications were filtered such that the global false discovery rate was a maximum of 1%. Protein abundance was calculated based on the three most abundant peptides (D'Arena G, et al. Am J Hematol. 2006; 81: 598-602).

Proteins with less than 2 unique peptides were excluded from further analysis.

Samples from 9 AC patients were analyzed, with healthy and cancerous lung tissues being taken from the same patient lung. In additional assay, healthy and cancerous lung tissues were taken from 5 AC and 5 SCC patients. Proteins for which at least two unique peptides were identified were used for further analysis.

Immunohistochemistry (IHC) on Tissue Microarray (TMA) Slides

Immunohistochemical staining was performed on formalin-fixed and paraffin-embedded tissue microarray slides obtained from Biomax US. The sections were deparaffinized using xylene and a graded ethanol series. Endogenous peroxidase activity was blocked by incubating the sections in 3% $H_2O_2$ for 10 minutes. Antigen retrieval was performed in 0.01M citrate buffer (pH 6.0) at 95° C.–98° C. for 20 min. After washing the sections in PBS (pH 7.4), non-specific antibody binding was reduced by incubating the sections in 10% normal goat serum for 2 h. After decanting excess serum, sections were incubated overnight at 4° C. with primary antibodies (Table 3). After washing with PBS, the sections were incubated for 2 h with the appropriate secondary antibodies conjugated to horseradish peroxidase (Table 3). Sections were washed three times in PBS and subsequently, the peroxidase-catalyzed reaction was visualized by incubation with 0.02% DAB. After rinsing in water, the sections were counterstained with hematoxylin, and mounted with Vectashield mounting medium (Vector Laboratories, Burlingame, Calif.). Finally, the sections were observed under a microscope (DM2500, Leica) and images were taken at the indicated magnification with the same light intensity and exposure time. Controls were carried out with the same protocols but omitting the primary antibodies.

Biomax Tissue Arrays

Cancer tissue microarrays were purchased from Biomax US (US Biomax). These included arrays for lung cancer (LC807,) containing lung normal tissues (n=10) and various lung cancer types in different stages, including AC (n=21), adenosquamous carcinoma (n=1), squamous cell carcinoma (SCC, n=31), bronchioloalveolar carcinoma (BAC; n=6), small cell carcinoma (n=6) and large cell carcinoma (n=5). Second tissue array (BC041115c) contained normal lung tissue (n=10), and AC (n=51) and SCC (n=41) cancerous tissue samples.

RNAseq Gene Expression Profiling

Data for the gene expression profile and for the heat map for healthy and tumor samples of lung cancer patients were obtained from XENA, TCGA [RNAseq using ployA+ Illumina HiSeq] (version 2016-08-16, TCGA hub, xena.ucsc.edu), with the unit being pan-cancer normalized (n=1,129). A linear fold of change and the statistical analysis were performed using a t-test.

Statistics and Bioinformatics Analysis

All descriptive statistics for data analysis were computed using the SPSS statistical package, version 17.0. Means±SEM of results obtained from the indicated independent experiments are presented. The level of significance of differences between the control (healthy) and experimental (cancer) groups was determined by non-parametric Mann-Whitney U test. A difference was considered statistically significant when the P value was deemed <0.05 (*), <0.01 () or <0.001 (*).

LC-HR-MS/MS data were imported into Partek Genomics Suite software (Partek, St. Louis, Mo.) and differences between expression levels of the proteins in the different groups were calculated using a t-test. Functional enrichment analysis of differentially expressed proteins was performed using the DAVID and Gene Ontology (GO) bioinformatics resources, v6.7 (Nawarak J, et al. Biochim Biophys Acta. 2009; 1794: 159-67).

Figure 1B:
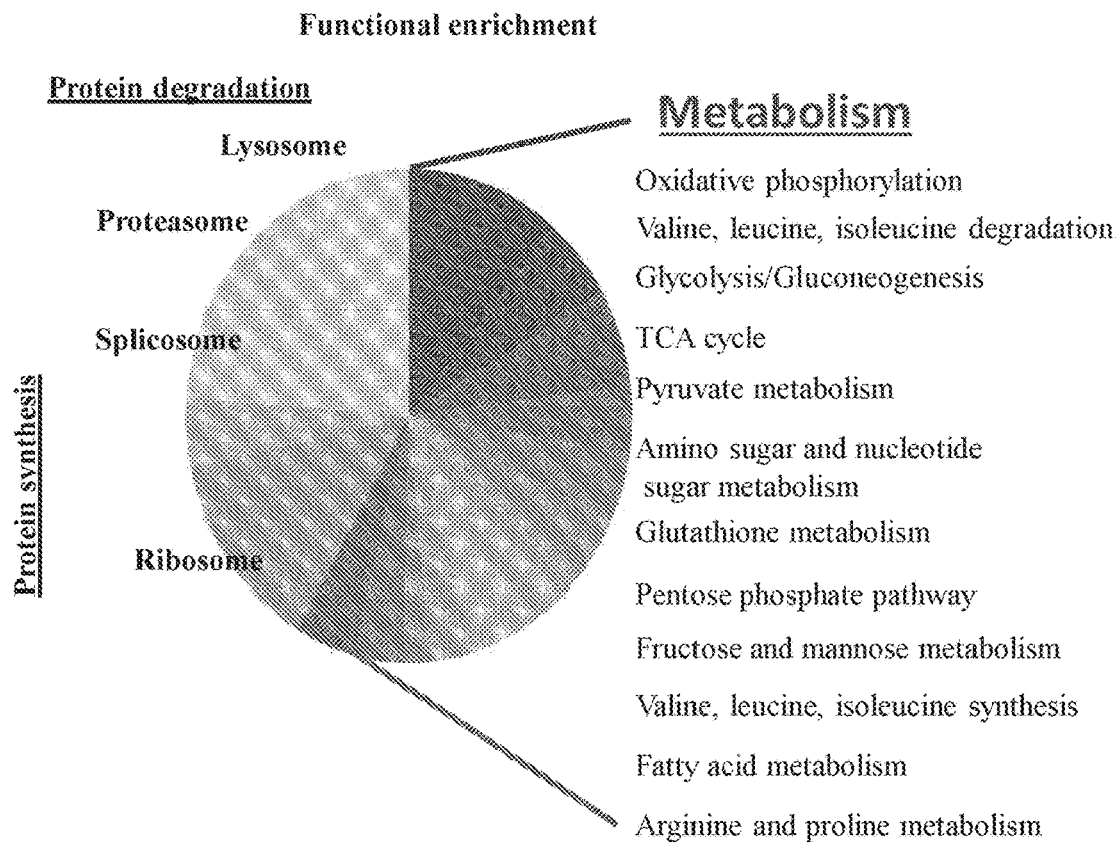
FIG. 1B: significantly enriched functional groups in the proteins showing changed expression, based on the Gene Ontology system.

Example 1: Mass Spectrometry Analysis of the Protein Profiles of Healthy and Tumor Tissues from NSCLC Patients To identify the proteins showing modified expression levels in NSCLC tumor tissues, relative to healthy tissues, nine samples of cancerous and healthy tissues were collected from the same lung of NSCLC patients and subjected to LC-HR MS/MS analysis. Hierarchical clustering based on the expression pattern of all detected proteins clearly allowed to distinguish between the healthy and tumor tissues (FIG. 1A), with the expression level of 1,494 proteins being changed (fold change (FC) ≥|2| and false discovery rate (FDR)<0.05, of which 378 proteins showed a FC≥|100|) (FIG. 1B). The up- and down-regulated proteins were further divided into two clusters, based on the combination of FC and p-value, due to some of the proteins being "absent" from some of the samples.

Next, functional analysis of the proteins differentially expressed between cancerous and healthy lung tissues was performed using the DAVID and Gene ontology databases (Ashburner M, et al. Gene ontology: tool for the unification of biology. The Gene Ontology Consortium. Nat Genet. 2000; 25: 25-9; Gene Ontology Consortium. Gene Ontology Consortium: going forward. Nucleic Acids Res. 2015; 43: D1049-56). Such analysis revealed enrichment of proteins related to protein synthesis and degradation, and in particular of proteins assigned roles in metabolism and to the mitochondria (FIG. 1C) (Table 6).

TABLE 6

Selected proteins differentially expressed in healthy donors and lung cancer patients identified by LC-HR MS/MS

| No | Protein name (Uniprot) | Fold change/P value | Proposed function (cell localization) | Relation to cancer |
|---|---|---|---|---|
| 1 | RB11B - Ras-related protein Rab-11B | >1000<br>$7.7 \times 10^{-12}$ | Regulator of intracellular membrane trafficking (Extracellular space, Endosome) | Over-expressed in HL-60 leukemia cell line |
| 2 | PIGS - GPI transamidase component PIG-S | >1000<br>$1.3 \times 10^{-9}$ | Component of the GPI transamidase complex (ER) | Over-expressed in breast, ovary and uterus cancers |
| 3 | APOOL - Apolipoprotein O-like | >1000<br>$2.1 \times 10^{-9}$ | Component of a large protein complex that functions in the maintenance of crista junctions (Mitochondria) | No reported data |

TABLE 6-continued

Selected proteins differentially expressed in healthy donors and lung cancer patients identified by LC-HR MS/MS

| No | Protein name (Uniprot) | Fold change/P value | Proposed function (cell localization) | Relation to cancer |
|---|---|---|---|---|
| 4 | NICA -Nicastrin | >1000<br>$5.8 \times 10^{-9}$ | A subunit of the gamma-secretase complex (Melanosome) | Regulates breast cancer stem cell properties and tumor growth |
| 5 | NDKB - Nucleoside diphosphate kinase B | 14.5<br>$3.1 \times 10^{-9}$ | Synthesis of nucleoside triphosphates other than ATP (Cytosol, Nucleus) | High expression reduce metastases in breast cancer, melanoma |
| 6 | HNRPL - Heterogeneous nuclear ribonucleoprotein L | 7.3<br>$1.3 \times 10^{-8}$ | Splicing factor, acting as activator or repressor of exon inclusion (Cytosol, Nucleus) | Marker for secondary to brain ALL metastasis |
| 7 | LDHA- L-lactate dehydrogenase A chain | 14.8<br>$2.3 \times 10^{-8}$ | Catalyzes the conversion of pyruvate to lactate and back (Cytosol) | Over-expressed in NSCLC, pancreas, colorectal cancer and more |
| 8 | STT3A - Dolichyl-diphospho-oligo saccharide-protein glycosyltransferase | 8.3<br>$1.2 \times 10^{-7}$ | Catalytic subunit of the N-oligosaccharyl transferase (OST) complex (ER) | Marker for follicular thyroid carcinoma |
| 9 | COPA - Coatomer subunit alpha | 14.6<br>$1.3 \times 10^{-7}$ | Part of a complex that mediates protein transport from the ER to the Golgi, (Cytosol, Golgi) | Associated with mouse mesothelioma progression |
| 10 | PDLI5 - PDZ and LIM domain protein 5 | 9.2<br>$1.8 \times 10^{-7}$ | Z-disc protein that interacts directly with a-actinin-2 (Cytosol, Cell junction) | Associated with gastric cancer. High deletion frequencies in oral squamous cell carcinoma. |
| 11 | HINT1- Histidine triad nucleotide-binding protein 1 | 5.4<br>$2.0 \times 10^{-7}$ | Hydrolyzes purine nucleotide phosphoramidates (Cytosol, Nucleus) | Over-expressed in prostate cancer |
| 12 | SEC11A - Signal peptidase complex catalytic subunit | >1000<br>$2.3 \times 10^{-7}$ | Component of a complex that removes signal peptides from proteins translocated into the ER (ER) | Contributes to malignant progression in gastric cancer |
| 13 | DDX6 - DEAD box protein 6 | 62.8<br>$2.5 \times 10^{-7}$ | Participates in mRNA degradation (Cytosol, Nucleus) | Chromosomal aberrations, DDX6 contribute to lymphomagenesis |
| 14 | PGK1 - Phosphoglycerate kinase 1 | 8.9<br>$3.2 \times 10^{-7}$ | Glycolytic enzyme, converting 3-phospho-D-glycerate to 3-phospho-D-glyceroyl phosphate (Cytosol) | Prognostic biomarker of poor survival and chemoresistance to paclitaxel treatment in breast cancer |
| 15 | IF4E - Eukaryotic transltion initiation factor 4E | 7.7<br>$3.5 \times 10^{-7}$ | Participates in the initiation of translation (Cytosol) | eIF4E over-expression can initiate malignant transformation |
| 16 | GDIB - Rab GDP dissociation inhibitor beta | 4.5<br>$3.9 \times 10^{-7}$ | Regulates the GDP/GTP exchange of most Rab proteins (Cytosol, Plasma membrane) | Increased in metastatic gallbladder cancer cell line SD18H and in pancreatic carcinoma |
| 17 | RL9 - 60S ribosomal protein L9 | 21.1<br>$4.5 \times 10^{-7}$ | Translation. Component of the 60S subunit (Cytosol) | Over-expressed in colon adenoma and adenocarcinoma |
| 18 | NDUS7 - ADH dehydrogenase (ubiquinone) iron-sulfur protein 7 | >1000<br>$4.7 \times 10^{-7}$ | Core subunit of the respiratory chain NADH dehydrogenase (Mitochondria) | Amplification in BRCA1-associated ovarian cancer |
| 19 | PTBP1 - Polypyrimidine tract-binding protein 1 | 8.4<br>$5.1 \times 10^{-7}$ | Plays a role in pre-mRNA splicing (Nucleus) | Over-expressed in colorectal cancer, gemcitabine resistance in pancreatic cancer, associated with breast tumorigenesis |
| 20 | CPNS1 - Calpain small subunit 1 | 11.8<br>$5.7 \times 10^{-7}$ | Regulatory subunit of the calcium-regulated thiol-rotease (Cytosol, Plasma membrane) | Promotes NSCLC progression, over-expressed in liver cancer, marker of poor prognosis in nasopharyngeal carcinoma |
| 21 | PA1B2 - Platelet-activating factor acetyl-hydrolase IB subunit beta | 9.9<br>$5.9 \times 10^{-7}$ | Inactivates PAF (platelet-activating factor) (Cytosol) | Important in maintaining cancer pathogenicity across a wide spectrum of cancer types |
| 22 | PPDX - Proto-porphyrinogen oxidase | >1000<br>$6.6 \times 10^{-7}$ | Catalyzes the oxidation of protoporphyrinogen-IX to form protoporphyrin-IX (Mitochondria) | Higher expression in faster growing cell lines and primary colorectal tumors |

TABLE 6-continued

Selected proteins differentially expressed in healthy donors and lung cancer patients identified by LC-HR MS/MS

| No | Protein name (Uniprot) | Fold change/P value | Proposed function (cell localization) | Relation to cancer |
|---|---|---|---|---|
| 23 | GBLP - Guanine nucleotide-binding protein subunit beta-2-like 1 | 5.8<br>$7.0 \times 10^{-7}$ | Intracellular receptor that binds activated PKC (Plasma membrane, Cytosol) | Over-expressed in NSCLC, breast cancer, hepatocellular carcinoma, esophageal squamous cell carcinoma |
| 24 | RL10 - 60S ribosomal protein L10a | 7.8<br>$7.1 \times 10^{-7}$ | Translation. Component of the 60S subunit (Cytosol) | Mutated in T-cell acute lymphoblastic leukemia |
| 25 | EN01 - Alpha-enolase | 9.7<br>$7.6 \times 10^{-7}$ | Glycolytic enzyme (Cytosol) | Upregulated in lung, brain, breast, colon cancers |
| 26 | ILF2 - Interleukin enhancer-binding factor 2 | 5.0<br>$7.7 \times 10^{-7}$ | Regulatory subunit of complexes involved in mitotic control, DNA break repair, and RNA splicing regulation (Cytosol Nucleus) | Higher expression in esophageal squamous cell carcinoma |
| 27 | ROA1 (HNRNPA1) - Heterogeneous nuclear ribonucleo-protein A1 | 5.6<br>$9.3 \times 10^{-7}$ | Involved in the packaging of pre-mRNA into hnRNP particles (Cytosol, Nucleus) | Biomarker in cervical carcinoma, lung cancer progression |
| 28 | VPS29- Vacuolar protein sorting-associated protein 29 | 14.7<br>$9.3 \times 10^{-7}$ | Component of the retromer cargo-selective complex (CSC) (Cytosol, Cell membrane, Endosome membrane) | No reported data |
| 29 | UGPA - UTP-glucose-1-phosphate uridylyltransferase | 7.7<br>$9.5 \times 10^{-7}$ | Glucosyl donor in cellular metabolic pathways (Cytosol) | Biomarker for metastatic hepatocellular carcinoma |
| 30 | DDX17- DEAD box protein 17 | 5.6<br>$1.2 \times 10^{-6}$ | RNA helicase, involved in transcription and splicing (Nucleus) | Increased expression in colon cancer |
| 31 | HAT1- Histone acetyltransferase type B catalytic subunit | 4.75<br>$4.4 \times 10^{-3}$ | Acetylates soluble histone H4 (nucleus), HAT1 is one of type B HAT members and functions in DNA repair. | High expression in several types of lymphomas. proposed indicator for a poor prognosis (Min SK, et al. Korean J Pathol. 2012; 46: 142-50) and potential drug target in esophageal SCC (Xue L, et al. Int J Clin Exp Pathol. 2014; 7: 3898-907) |
| 32 | RS3 - 40S ribosomal protein S3 | 9.4<br>$1.2 \times 10^{-6}$ | Translation. Component of the 40S subunit (Cytosol, Nucleus) | Proposed as an indicator of malignant tumors, over-expressed in colorectal cancer, under-expressed SCC |
| 33 | OSBL8 - Oxysterol-binding protein-related protein 8 | >1000<br>$1.2 \times 10^{-6}$ | Binds 25-hydroxycholesterol and cholesterol (ER membrane, Nucleus membrane) | Down-regulated in hepatoma tissues |
| 34 | TXD12 (ERp19) - Thioredoxin domain-containing protein 12 | 37.6<br>$1.4 \times 10^{-6}$ | Involved in thiol-disulfide oxidase activity (ER) | A thioredoxin-like protein, implicated in development of breast, ovarian, gastrointestinal and gastric cancers |
| 35 | USO1 - General vesicular transport factor p115 | 8.7<br>$1.4 \times 10^{-6}$ | General vesicular transport factor in Golgi (Cytosol, Golgi) | Promotes proliferation of gastric cancer cells |
| 36 | COPB2 - Coatomer subunit beta 2 | 12.0<br>$1.4 \times 10^{-6}$ | Involved in protein transport from the ER to the Golgi (Cytosol, Golgi) | Over-expressed (mRNA) in lung adenocarcinoma tumors |
| 37 | SMD3 - Small nuclear ribonucleoprotein Sm D3 | 9.0<br>$1.4 \times 10^{-6}$ | Core component of the spliceosome (Cytosol, Nucleus) | Associated with metastatic behavior is soft tissue tumors |
| 38 | ITB2 - Integrin beta-2 | 5.9<br>$1.5 \times 10^{-6}$ | Cell adhesion (Plasma membrane, Exosome) | Over-expressed in CLL patients harboring trisomy 12 |
| 39 | COPB1 - Coatomer subunit beta 1 | 6.5<br>$1.5 \times 10^{-6}$ | Involved in protein transport from the ER to the Golgi (Cytosol, Golgi) | Over-expressed in prostate cancer |

TABLE 6-continued

Selected proteins differentially expressed in healthy donors and lung cancer patients identified by LC-HR MS/MS

| No | Protein name (Uniprot) | Fold change/P value | Proposed function (cell localization) | Relation to cancer |
|---|---|---|---|---|
| 40 | MYH9 - myosin 9 | 6.5<br>$1.7 \times 10^{-6}$ | Motor protein (Cytosol) | Highly expressed in CL16 breast cancer cell tumors in mice |
| 41 | RAGE - Receptor for advanced glycol-sylation end products | -12.2<br>$1.9 \times 10^{-6}$ | Binds advanced glycation end products (Plasma membrane, Extracellular space) | Polymorphism associated with susceptibility to renal, lung and gastric cancers |
| 42 | VDAC1 - voltage dependent anion channel 1 | 6.3<br>$2.2 \times 10^{-6}$ | Channel transporting ions and metabolites, also involved in apoptosis (Mitochondria) | Over-expressed in CLL and lung cancer, predictor of poor outcome in early stage NSCLC |
| 43 | ENPL (HSP90B1) - Endoplasmin | 7.3<br>$2.3 \times 10^{-6}$ | Chaperone that functions in the processing and transport of secreted proteins (ER, Melanosome) | Up-regulated (mRNA) in lung cancer. Down-regulated in non-cancer stroma cells from colon cancer tissues |
| 44 | CAF17 - Iron-sulfur cluster assembly factor homolog | >1000<br>$2.5 \times 10^{-6}$ | Involved in the maturation of mitochondrial 4Fe-4S proteins, (Mitochondria) | No reported data |
| 45 | PSME3 - Proteasome activator complex subunit 3 | >1000<br>$2.6 \times 10^{-6}$ | Subunit of the 11S REG proteasome regulator (Cytosol, Nucleus) | Serum tumor marker for colorectal cancer |
| 46 | TM9S3 - Transmembrane 9 superfamily member 3 | 11.3<br>$2.6 \times 10^{-6}$ | Belongs to nonaspanin protein family. Function not known (Plasma membrane, Golgi) | Diagnostic and therapeutic target for scirrhous-type gastric cancer. Breast cancer chemoresistance factor |
| 47 | THY1 - Thy-1 membrane glycoprotein | 8.5<br>$2.9 \times 10^{-6}$ | Proposed to function in cell-cell or cell-ligand interactions (Plasma membrane) | Marker for lung, liver, glioma and breast cancer stem cells |
| 48 | RS3A - 40S ribosomal protein S3a | 11.8<br>$3.3 \times 10^{-6}$ | Translation, component of the 40S subunit (Cytosol, Nucleus) | Marker for human squamous cell lung cancer |
| 49 | MMP19 - Matrix metalloproteinase-19 | >1000<br>$3.3 \times 10^{-6}$ | Endopeptidase that degrades various components of the extracellular matrix (ECM) | Involved in NSCLC metastasis and associated with increased mortality |
| 50 | ARPC3 - Actin-related protein 2/3 complex subunit 3 | 8.6<br>$4.2 \times 10^{-6}$ | Component of the Arp2/3 complex involved in regulation of actin polymerization (Cytosol) | Associated with glioma |
| 51 | RS15 - 40S ribosomal protein S15 | 15.9<br>$4.3 \times 10^{-6}$ | Translation, component of the 40S subunit (Cytosol, Nucleus) | RS15 mutations are associated with increased cancer risk |
| 52 | PRKDC - DNA-dependent protein kinase catalytic subunit | 10.1<br>$4.5 \times 10^{-6}$ | Serine/threonine-protein kinase that acts as a molecular sensor for DNA damage (Nucleus) | Highly expressed in advanced neuroblastoma, associated with gastric carcinoma |
| 53 | RPN2 - Ribophorin II | 8.8<br>$4.5 \times 10^{-6}$ | Protein glycosylation. Essential subunit of the N-oligosaccharyl transferase (OST) complex (ER Plasma membrane) | Breast cancer initiation and metastasis, associated with docetaxel response in oesophageal SCC |
| 54 | RBMX - RNA-binding motif protein, X chromosome | 6.1<br>$4.4 \times 10^{-6}$ | RNA-binding protein that plays several roles in the regulation of pre- and post-transcriptional processes (Nucleus) | Up-regulated in immortalized cells, cancer cells, and NSCLC tissues |
| 55 | ANM1 - Protein arginine N-methyltransferase 1 | 6.2<br>$4.9 \times 10^{-6}$ | Arginine methyltransferase (Cytosol, Nucleus) | Over-expressed in NSCLC cell lines, proposed as a marker in breast cancer |
| 56 | MAP2K1 (MEK1) - Dual specificity mitogen-activated protein kinase 1 | 165.3<br>$5.7 \times 10^{-3}$ | A component of the MAP kinase signal transduction pathway, binds extracellular ligands, activates RAS and RAF1 (Cytosol) | Over-expressed in NSCLC |
| 57 | EGFR - Epidermal growth factor receptor | 92.6<br>$1 \times 10^{-2}$ | Receptor tyrosine kinase binding ligands of the EGF family (Cell membrane, ER, Golgi, Nucleus) | Over-expressed in NSCLC |

TABLE 6-continued

Selected proteins differentially expressed in healthy donors and lung cancer patients identified by LC-HR MS/MS

| No | Protein name (Uniprot) | Fold change/P value | Proposed function (cell localization) | Relation to cancer |
|---|---|---|---|---|
| 58 | HYOU1- Hypoxia up-regulated protein-1 | −2.7<br>0.032 | A chaperon molecule belongs to HSP70 family, induced by hypoxia, has cytoprotective activity (ER) | Over-expressed in NSCLC (Fahrmann JFet al. Clin Proteomics. 2016; 13: 31) |
| 59 | LRRFIP2- leucine-rich repeat flightless-interacting protein 2 | 19.3<br>$2.9 \times 10^{-2}$ | Positive regulator of the Toll-like receptor (TLR) signaling (cytoplasm) | No reported data |
| 60 | WDR82- WD repeat-containing protein 82 | 9.8<br>$3.1 \times 10^{-2}$ | Component of histone methyl-transferase complex (nucleus) | No reported data |
| 61 | AKR1B10- aldo-keto reductase family 1 member B10 | 17.9<br>$1.9 \times 10^{-3}$ | Regulates the balance of retinoic acid and lipid metabolism (lysosome, secreted) | Potential diagnostic marker specific to smokers NSCLCs (Fukumoto S, et al. Clin Cancer Res. 2005; 11: 1776-85) |
| 62 | TTL12- tubulin-tyrosine ligase-like protein 12 | 8.1<br>$2.1 \times 10^{-3}$ | Catalyze posttranslational modification of tubulins (cytoplasm) | Expression increases during cancer progression to metastasis of prostate cancer (Wasylyk C, et al. Int J Cancer. 2010; 127: 2542-53) |
| 63 | ACOT1- Acyl-co-enzyme A thioesterase 1 | −2.8<br>$5.6 \times 10^{-3}$ | Long chain fatty acid metabolism (Cytoplasm) | Highly expressed in luminal breast tumors (Hill JJ, et al. J Proteome Res. 2015; 14: 1376-88) |
| 64 | TSG101- tumor susceptibility gene 101 protein | −38.3<br>$2.6 \times 10^{-3}$ | regulator of vesicular trafficking process (mainly cytoplasmic) | TSG101 splicing variant is linked to progressive tumor-stage and metastasis (Chua HH, et al. Oncotarget. 2016; 7: 8240-52) |
| 65 | RAB34- Ras-related protein Rab-34 | −6.0<br>$7.6 \times 10^{-3}$ | GTPase involved in protein transport (Cytoplasm, Golgi) | RAB34 is a progression- and prognosis-associated biomarker in gliomas (Wang HJ, et al.Tumour Biol. 2015; 36: 1573-8);Ras association sarcomagenesis (Galoian K, et al. Tumour Biol. 2014; 35: 483-92 |
| 66 | ITGA7-integrin alpha-7 | 107.3<br>$1.3 \times 10^{-3}$ | Laminin receptor on skeletal myoblasts (plasma membrane) | Associated with the occurrence and development of bladder cancer (Jia Z, et al. Tumori. 2015; 101: 117-22) |
| 67 | GALE - UDP-galactose-4-epimerase | 2.18 | Catalyzes two distinct but analogous reactions: the epimerization of UDP-glucose to UDP-galactose, and the epimerization of UDP-N-acetylglucosamine to UDP-N-acetylgalactosamine | Overexpressed in thyroid papillary carcinoma (da Silveira Mitteldorf CAlet al. Diagn Cytopathol. 2011 Aug; 39(8):556-61) |
| 68 | ACAD8- acyl-CoA dehydrogenase family member 8 | 11.4 | Catalyze the dehydrogenation of acyl-CoA derivatives in the metabolism of fatty acids or branch chained amino acids | No reported data |

Table 6 above is based on two independent LC-HR MS/MS experiments that were performed as described hereinabove. From each experiment, differentially expressed proteins (p-value <0.01, FC≥|2|) were filtered and proteins differentially expressed in both experiments were selected. Proteins of relevance to lung cancer or with potential as biomarkers are listed. For each protein, the name, fold change and p-value as well as its function, sub-cellular localization and relevance to cancer are indicated.

Example 2: Modified Expression of Metabolism- and Apoptosis-Related Proteins

Figure 2A:
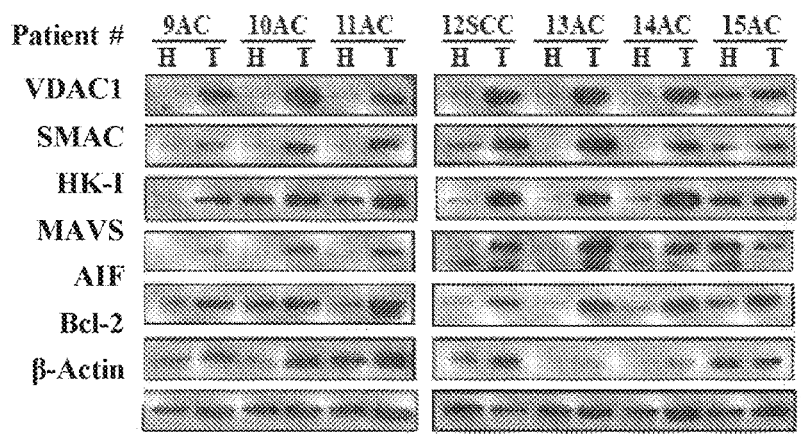
FIG. 2A: representative immunoblots of tissue lysates of tumor (T) and healthy (H) lung tissues derived from lung cancer patients probed with antibodies directed against VDAC1, SMAC, HK-I, MAVS, AIF and Bcl-2.
Figure 2B:
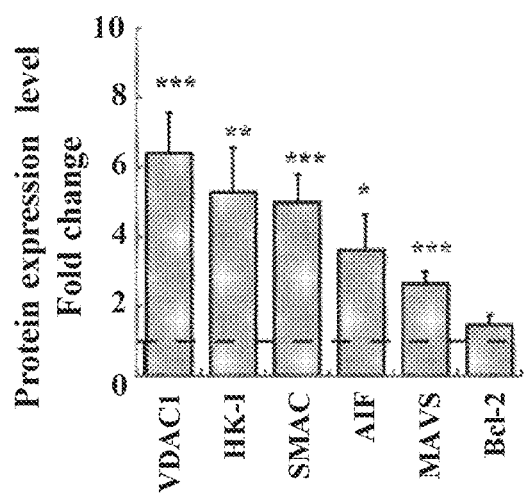
FIG. 2B: quantitative analysis of VDAC1 (37 patients, fold cgnage (FC)=6.2, p-value=$5\times10^{-5}$); SMAC (37 patients, FC=5, p-value=$3.4\times10^{-5}$); HK-I, (33 patients, FC=5.3, p-value=$5.3\times10^{-3}$); MAVS (22 patients, FC=2.6, p-value=$1.5\times10^{-4}$); AIF (35 patients, FC=3.5, p-value=$1.7\times10^{-2}$), and Bcl-2 (22 patients, FC=1.5, p-value=$1.4\times10^{-1}$) are presented as the mean±SD.
Figure 2C:
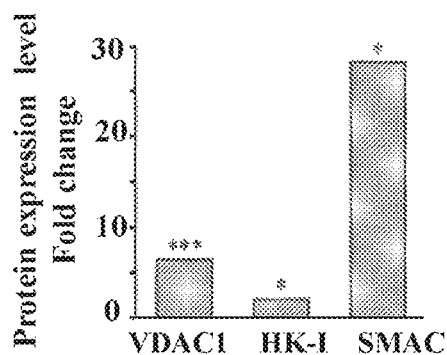
FIG. 2C: LC-HR MS/MS data for VDAC1, HK1 and SMAC. A difference between healthy and tumor tissues was considered statistically significant when $P<0.001$ (*), $P<0.01$ (), $P<0.05$ (*), as determined by the Mann-Whitney test for the immunoblots and a two-way t-test for the LC-HR MS/MS data.
Figure 2D:
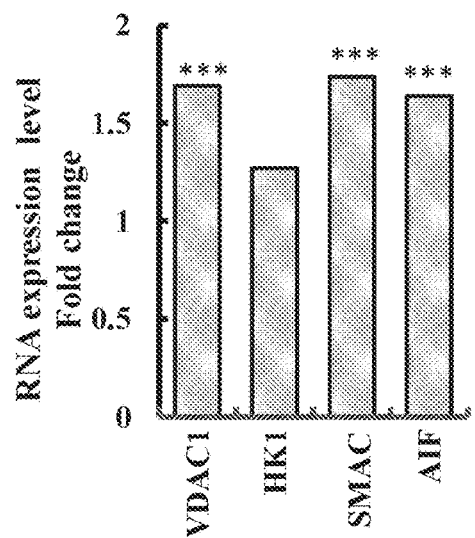
FIG. 2D: quantitative analysis of gene expression based on RNAseq of VDAC1, HK-I, SMAC and AIF. The gene expression profiles was obtained from publicly available data (TCGA lung cancer dataset) for healthy (n=110) and tumor lung samples (n=1,017) of lung cancer patients.
Figure 2E:
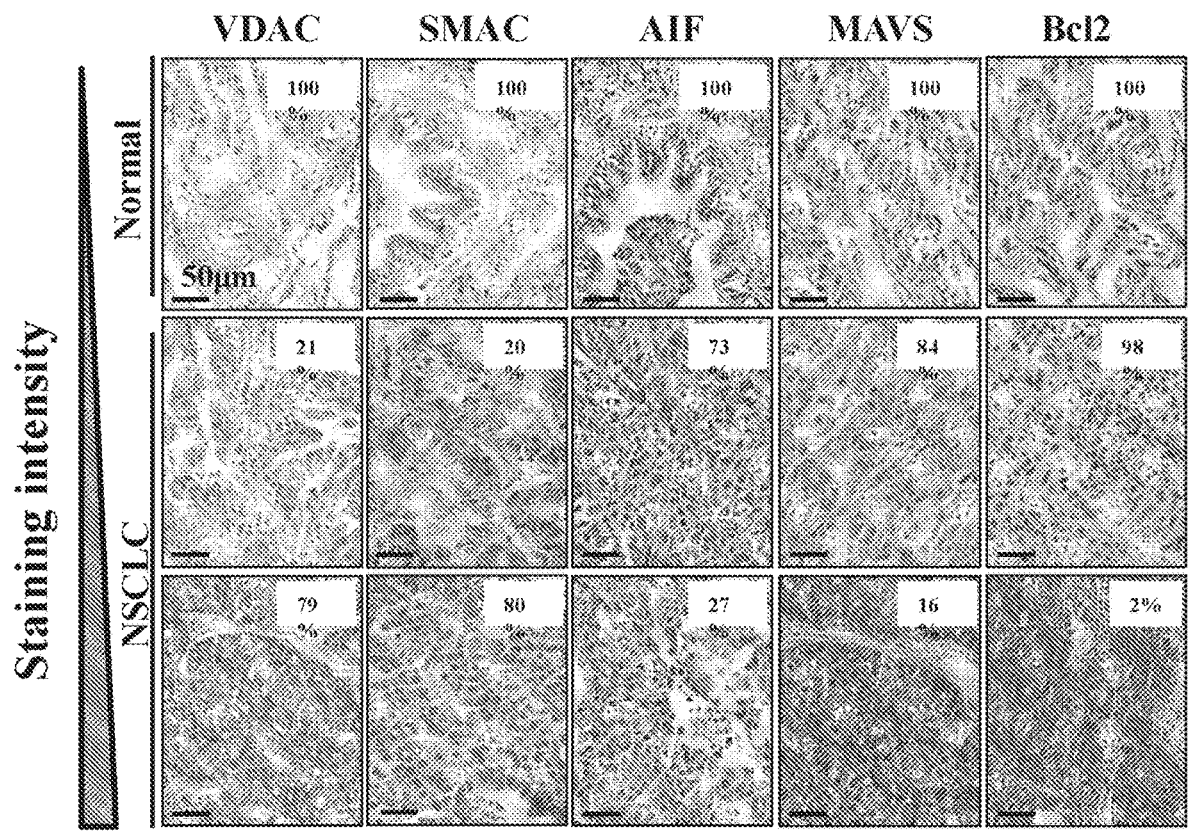
FIG. 2E: overexpression of VDAC1, SMAC, AIF, MAVS and Bcl-2 in lung cancer patients. Representative IHC staining for VDAC1, SMAC AIF, MAVS and Bcl-2 of normal (n=5) and lung cancer (n=20) tissue samples from tissue microarray slides (Biomax). The percentages of patient samples that stained at the indicated intensity are shown

Modified metabolism and the development of anti-apoptotic mechanism are hallmarks of cancer. As previously described (WO 2013/035095) several proteins associated with these hallmarks are overexpressed in certain types of cancer. Samples of tumor and healthy tissues from the same lung of NSCLC patients were analyzed by immunoblotting using specific antibodies to assess levels of the voltage-dependent anion channel 1 (VDAC1), hexokinase I (HK-I), SMAC/Diablo (SMAC), Apoptosis inducing factor (AIF), mitochondrial anti-viral signaling (MAVS) and Bcl2 (FIG. 2). All of these proteins, with the exception of Bcl2, were significantly over-expressed (3- to 6-fold) in cancerous tissues as compared to a healthy tissues obtained from the same NSCLC patient (FIG. 2A, B). LC-HR-MS/MS further confirmed that expression levels of VDAC1, HK-I and SMAC were highly increased in cancer tissue (FIG. 2C). The RNA expression levels of VDAC1, HK-I, SMAC and AIF showed a similar trend, although expression at the RNA level was lower, as revealed from the RNAseq gene expression profiling data (FIG. 2,E).

The expression levels of VDAC1, SMAC, AIF, HK-I, MAVS and Bcl2 was also analyzed by IHC in tissue microarrays comprising normal and NSCLC derived samples (FIG. 2F). All proteins were highly expressed in the tumor tissue. Thus, although SMAC, AIF are pro-apoptotic proteins, they are over-expressed in tumor tissue.

Other metabolism-related proteins, such as lactate dehydrogenase (LDHA), the ATP synthase subunit 5B (ATP5B), the glycolysis enzyme glyceraldehyde 3 phosphate dehydrogenase (GAPDH), phosphoglycerate kinase 1, (PGK1) and enolase-1 (ENO1), were also highly expressed (up to 14-fold higher) in the tumor tissues, as determined by LC-HR-MS/MS analysis (FIG. 3A, D,E).

These results point to the significance of reprogrammed metabolism and apoptosis avoidance in lung cancer.

Example 3: Identification of Bio-Markers of Lung Cancer

LC-HR-MS/MS analysis data revealed many other proteins that were differentially expressed in the NSCLC tumors (Table 6). The proteins with the most significant changes in expression in the tumors are presented along with their proposed function and relation to cancer in Table 6. These include Ras-related protein Rab11B (Rab11B), a member of the Ras superfamily of small GTP-binding proteins, HYOU1 (ORP150), which plays a pivotal role in cytoprotective cellular mechanisms triggered by oxygen deprivation, and the heat-shock protein HSPD1 (HSP60). These findings were confirmed by immunoblot analysis, the RNAseq UCSC XENA data and qRT-PCR (FIG. 3).

Network analysis of the proteins identified here by proteomics (and confirmed by the immunoblot analysis, the RNAseq gene expression profiling data and qRT-PCR) demonstrated that most of these proteins interact at several levels, with metabolic processes-related proteins being central. These interactions include common functionality associated with cell metabolism, and involved direct physical interaction with each other. Many of these proteins are co-expressed and may therefore be defined as a cluster that is regulated by epigenetic modifications.

Example 4: Proteins Differentially Expressed in AC and SCC

Analysis of lung tissue microarrays for VDAC1 and AIF (from 10 healthy, 31 SCC and 17 AC samples) and for SMAC/Diablo (from 20 healthy, 72 SCC and 72 AC samples) expression levels by IHC staining using specific antibodies revealed high expression of these proteins in lung cancer, as compared to healthy tissue (FIG. 4A). Quantity analyses of the IHC results, presented as the number of patient samples showing staining at the indicated intensity and represented as a percentage of the total number of section analyzed, showed that VDAC1, SMAC and AIF expression levels were higher in SCC than in AC (FIG. 4A).

Next, cancerous and healthy tissues samples from the lung of five of each AC and SCC patients were subjected to LC-HR-MS/MS analysis. The expression levels of 2,959 proteins were up- or down-regulated in the cancerous tissues relative to the expression in the corresponding healthy tissue, with the change in expression of 1,513 proteins being significant. The proteins showing the highest change in the expression levels (p-value <0.01) between the two NSCLC sub-types were selected and the fold change of expression in the tumor relative to the healthy tissue was calculated and presented as the SCC/AC ratio for each protein (FIG. 4B). Assessing the SCC/AC ratios revealed that HAT1, ITGA7, LRRFIP2, AKR1B10 (secreted protein), WDR82, TTLL12, and USP14 were highly over-expressed (up to 500-fold) in SCC, as were VDAC1 and SMAC to a lower extent, while HYOU1, ACOT1, RAB34, and TSG101 showed higher expression in AC. Table 7 presents the fold change in the expression of each of these and additional proteins in lung samples obtained from patients with NSCLC subtype AC or SCC compared to the expression in lung samples of healthy subject or healthy lung tissues. Further presented is the SCC to AC expression ratio, the proposed function of the protein and its relation to cancer.

TABLE 7

Biomarkers for differentiating between NSCLC subtype AC and SCC

| Uniport Gene Name | AC Fold of change Tumor/Healthy | SCC Fold of change Tumor/Healthy | Ratio SCC/AC (p value) | Proposed function (cell localization) | Relation to cancer |
|---|---|---|---|---|---|
| HAT1-Histone acetyltransferase type B catalytic subunit (014929) | −23.66 | 20.09 | 476 $4.4 \times 10^{-3}$ | Acetylates soluble histone H4, a type B HAT that functions in DNA repair (Nucleus) | High expression in several types of lymphomas. Proposed indicator for poor prognosis and potential drug target in esophageal SCC (Cho SJ, et al. Korean J Pathol. 2012; 46: 142-50; Xue L, et al. Int J Clin Exp Pathol. 2014; 7: 3898-907) |
| LRRFIP2-Leucine-rich repeat flightless- | −7.83 | 2.47 | 19.3 $2.9 \times 10^{-3}$ | Positive regulator of the Toll-like receptor (TLR) | No reported data |

TABLE 7-continued

Biomarkers for differentiating between NSCLC subtype AC and SCC

| Uniport Gene Name | AC Fold of change Tumor/Healthy | SCC Fold of change Tumor/Healthy | Ratio SCC/AC (p value) | Proposed function (cell localization) | Relation to cancer |
|---|---|---|---|---|---|
| interacting protein 2 (Q9Y608) | | | | signaling (Cytosol) | |
| AKR1B10- Aldo-keto reductase family 1 member B10 (O60218) | −1.79 | 10.03 | 17.9<br>$1.9 \times 10^{-3}$ | Regulates the balance of retinoic acid and lipid metabolism (lysosome, Secreted) | Potential diagnostic marker specific to smokers NSCLCs (Fukumoto S, et al. Clin Cancer Res. 2005; 11: 1776-85). |
| WDR82- WD repeat-containing protein 82 (Q6UXN9) | −2.15 | 4.56 | 9.81<br>$3.1 \times 10^{-3}$ | Component of histone methyl-transferase complex (Nucleus) | No reported data |
| TTLL12- Tubulin-tyrosine ligase-like protein 12 (Q14166) | −1.69 | 4.82 | 8.14<br>$2.1 \times 10^{-3}$ | Catalyze post-translational modification of tubulins (Cytosol) | Expression increases during prostate cancer progression to metastasis (Wasylyk C, et al. Int J Cancer. 2010; 127: 2542-53) |
| IGF2BP3- Insulin-like growth factor 2 mRNA-binding protein (O00425) | −1.35 | 3.65 | 4.93 | RNA-binding factor that may recruit target transcripts to cytoplasmic protein-RNA complexes (mRNPs)(Nucleus, Cytosol) | Associated with NSCLC (Shi R, et al. Tumour Biol. 2017; doi.org/10.1177/101042 8317695928) |
| SMC2 - Structural maintenance of chromosomes protein 2 (O95347) | −1.56 | 1.34 | 2.09 | Involved in condensing chromatin complex (Cytosol, Nucleus) | No reported data |
| ACOT1- Acyl-co-enzyme A thioesterase 1 (Q86TX2) | 1.34 | −2.09 | −2.8<br>$5.6 \times 10^{-3}$ | Long chain fatty acid metabolism (Cytosl) | Highly expressed in luminal breast tumors (Hill JJ, et al. J Proteome Res. 2015; 14: 1376-88) |
| ACAD8 - Isobutyryl-CoA dehydrogenase (Q9UKU7) | 11.4 | −1.42 | −16.1 | Acyl-CoA dehydrogenase, catabolism of valine (Mitochondria) | No reported data |
| GALE - UDP-glucose 4-epimerase (Q14376) | 2.18 | −1.33 | −2.91 | Galactose metabolism (Cytosol, Exosomes) | No reported data |
| RSU1 - Ras suppressor protein 1 (Q15404) | 1.05 | −3.98 | −4.29 | Ras signal transduction pathway (Cytosol, Exosomes) | No reported data |
| HY0U1 Hypoxia up-regulated protein 1 | 1.67 | −1.59 | −2.7 | A chaperon molecule belongs to HSP70 family, induced by hypoxia, has cytoprotective activity (ER) | Over-expressed in NSCLC |
| USP14- Ubiquitin carboxyl-terminal hydrolase 14 (P54578) | 1.26 | 5.58 | 4.43<br>$2.0 \times 10^{-3}$ | Proteasome-associated deubiquitinase (Cytosol, Plasma membrane) | Over-expressed in various types of cancer including NSCLC (Zhu Y, et al. Cell Physiol Biochem. 2016; 38: 993-1002). |
| ITGA7- Integrin alpha-7 (Q13683) | 4.17 | 447.21 | 107.2<br>$1.3 \times 10^{-3}$ | Laminin receptor on skeletal myoblasts (Plasma membrane) | Associated with the occurrence and development of bladder cancer (Jia Z, et al. Tumori. 2015; 101: 117-22 |
| TSG101- Tumor susceptibility | 165.38 | 4.32 | −38.5<br>$2.6 \times 10^{-3}$ | Regulator of vesicular | TSG101 splicing variant is linked to |

TABLE 7-continued

Biomarkers for differentiating between NSCLC subtype AC and SCC

| Uniport Gene Name | AC Fold of change Tumor/Healthy | SCC Fold of change Tumor/Healthy | Ratio SCC/AC (p value) | Proposed function (cell localization) | Relation to cancer |
|---|---|---|---|---|---|
| gene 101 protein (Q99816) | | | | trafficking process (Plasma membrane, Cytosol, Nucleus) | progressive tumor-stage and metastasis (Chua HH, et al.. Oncotarget. 2016; 7: 8240-52) |
| RAB34— Ras-related protein Rab-34 (Q9BZG1) | −1.16 | −7.05 | −6.08 $7.6 \times 10^{-3}$ | GTPase involved in protein transport (Cytosol, Golgi) | A progression- and prognosis-associated biomarker in gliomas (Wang HJ, et al. Tumour Biol. 2015; 36: 1573-8). Ras-associated sarcomagenesis (Galoian K, et al. Tumour Biol. 2014; 35: 483-92) |

The expression of several of the proteins showing significant differential expression (MS/MS data, FIG. 4B), and of NAPSA (previously proposed for distinguishing between AC and SCC) was analyzed using RNAseq (UCSC XENA, n=1,129) on tissues obtained from healthy and lung cancer patients (FIG. 5A). The analysis revealed that ACOT1, RAB34, TSG101, and NAPSA RNA expression level was lower in SCC than in AC, while the RNA expression level of SMAC, AKR1B10 (a secreted protein), HAT1, USP14, and TTLL12, and to a lesser extent of WDR82 and VDAC1, was higher in SCC relative to the expression in AC. These results are in agreement with the proteomics data (FIG. 4B), and thus propose the use of these proteins and/or RNA encoding them as markers to distinguish between AC and SCC.

In an attempt to identify additional proteins having modified expression in NSCLC as revealed in the proteomics data, which can differentiate between AC and SCC, the RNA levels of several proteins was determined using RNAseq UCSC XENA data (FIG. 5B). The RNA level encoding for TP63, GGH (secreted protein), Ck5, Ck13, Ck14, Ck17, CSTA, RANBP1, TIMM44 FEN1, FEN2, SMC2, and IGF2BP3 were increased in SCC relative to AC, while the level of RNA encoding for RSU1, AKR7A3, GALE, AZGP1 (secreted protein), ACOT1, ABCD3, NPC2 (secreted protein), ACAD8, RPS6KA3, ARRB1 and LRBA showed the opposite trend, namely higher expression in AC relative to SCC. The functions of the products of these genes and previously reported relation to AC or SCC are listed in Table 8.

TABLE 8

Proteins encoded by RNA differentially expressed in SCC and AC

| Gene | Proposed function (cell localization) | Relation to NSCLC |
|---|---|---|
| Higher RNA expression levels in AC | | |
| 1. AZGP1 - Zinc-alpha-2-glycoprotein (P25311) | Lipid degradation in adipocytes, associated with fat losses in some advanced cancers (Plasma membrane, Secreted, Exosomes) | Associated with AC lung cancer (Falvella FS, et al. Oncogene. 2008; 27: 1650-6) |
| 2. ACOT1 - Acyl-coenzyme A thioesterase 1 (Q86TX2) | Lipid metabolism, long chain fatty acid metabolism (Cytosol) | No reported data |
| 3. ACAD8 - Isobutyryl-CoA dehydrogenase (Q9UKU7) | Acyl-CoA dehydrogenase, catabolism of valine (Mitochondria) | No reported data |
| 4. NPC2 - Epididymal secretory protein E1 (P61916) | Cholesterol transporter (ER, Lysosome, Secreted) | Associated with lung AC (Pernemalm M, et al. Proteomics. 2009; 9: 3414-24) |
| 5. ABCD3 - ATP-binding cassette sub-family D member 3 (P28288) | Involved in fatty acid transport (Peroxisome) | Associated with lung AC (Tran QN. BMC Med Genomics. 2013; 6: S11) |
| 6. GALE - UDP-glucose 4-epimerase (Q14376) | Galactose metabolism (Cytosol, Exosomes) | No reported data |
| 7. FEN1 - Flap endonuclease 1 (P39748) | Endonuclease involved in DNA replication and repair (Cytosol) | Associated with lung AC (Hwang JC, et al. PLoS One. 2015; 10: e0139435) |
| 8. AKR7A3 - Aldo-Keto Reductase family 7A isoform 3 (O95154) | Invoved in Aflotoxin B1 inactivation (Cytosol, Exosome) | No reported data |
| 9. ARRB1 - Beta-arrestin-1 (P49407) | Signaling pathway: Functions in regulating agonist-mediated GPCR | Enhances chemosensitivity in NSCLC) (Shen H, et al. Oncol Rep. 2017; 37: 761-7) |

TABLE 8-continued

Proteins encoded by RNA differentially expressed in SCC and AC

| Gene | Proposed function (cell localization) | Relation to NSCLC |
|---|---|---|
| 10. RSU1 - Ras suppressor protein 1 (Q15404) | Ras signal transduction pathway (Cytosol, Exosomes) (Membrane, Cytosol, Nucleus) | No reported data |
| 11. LRBA - Lipopoly-saccharide-responsive and beige-like anchor protein (P50851) | Coordinates signaling of immune receptors (Cell membrane, ER, Golgi, Lysosome) | No reported data |
| Higher expression RNA levels in SCC | | |
| 12. Ck5 - Keratin, type II cytoskeletal 5 (P13647) | Structural protein (Plasma membrane, Cytosol, Nucleus, Exosome) | Associated with lung SCC (Vogt AP, et al. Diagn Cytopathol. 2014; 42: 453-8; Chen Y, et al. Oncology. 2011; 80: 333-40) |
| 13. Ck13 - Keratin, type I cytoskeletal 13 (P13646) | Structural protein (Cytosol, Nucleus, Exosome) | Associated with lung SCC (Lee M-S, et al. Oncotarget. 2016; 7: 36101-14) |
| 14. Ck14 - Keratin, type I cytoskeletal 14 (P02533) | Structural protein (Cytosol, Nucleus) | Associated with lung SCC (Chen et al., 2011, ibid; Nakanishi Y, et al. Acta Histochem Cytochem. 2013; 46: 85-96) |
| 15. Ck17 - Keratin, type I cytoskeletal 17 (Q04695) | Structural protein (Cytosol) | Associated with lung SCC (Chen et al., 2011, ibid) |
| 16. PFN2 - Profilin-2 (P35080) | Structural protein (Cytosol) | Associated with NSCLC (Tang YN, et al. Nat Commun. 2015; 6: 8230) |
| 17. RANBP1 - Specific GTPase- activating protein (P43487) | Signaling pathway, Inhibits GTP exchange on Ran (Cytosol, Nucleus) | No reported data |
| 18. CSTA - Cystatin-A (P01040) | Thiol proteinase inhibitor (Cytosol, Exosomes) | Associated with lung SCC (Butler MW, et al. Cancer Res. 2011; 71: 2572-81; Leinonen T, et al. J Clin Pathol. 2007; 60: 515-9) |
| 19. GGH - Gamma-glutamyl hydrolase (Q92820) | Amino acid metabolism, Hydrolyzes polyglutamate (Lysosome, Secreted) | Associated with lung cancer (NSCLC) (Yoshida T, et al. Anticancer Res. 2016; 36: 6319-26) |
| 20. TIMM44 - Mitochondrial IMM translocase subunit TIM44 (O43615) | Mitochondrial peptide transporter, essential component of the PAM complex, ATP binding (Mitochondria) | No reported data |
| 21. TP63 - Tumor protein 63 (Q9H3D4) | Tumor suppressor (Nucleus) | Associated with lung SCC (Vogt et al. 2014, ibid) |
| 22. SMC2 - Structural maintenance of chromosomes protein 2 (O95347) | Involved in condensing chromatin complex (Cytosol, Nucleus) | No reported data |
| 23. IGF2BP3 Insulin-like growth factor 2 mRNA-binding protein | RNA-binding factor that may recruit target transcripts to cytoplasmic protein-RNA complexes (mRNPs)(Nucleus, Cytosol) | Associated with NSCLC (Shi R, et al. Tumour Biol. 2017; doi.org/10.1177/1010428317695928) |
| RPS6KA3- Ribosomal protein S6 kinase alpha-3 (P51812) | Serine/threonine-protein kinase acts downstream of ERK signaling (Nucleus, Cytosol) | Associated with NSCLC (Song R, et al. BMC Genomics. 2014; 15: S16; Tan Q, et al. Onco Targets Ther. 2013; 6: 1471-9) |

Example 5: Expression of Proteins Associated with Survival Rates in AC and SCC

To further test the prognostic value of the proteins proposed to distinguish between AC and SCC, survival analysis was performed on public-available gene expression datasets of lung cancer patients. A Kaplan-Meier analysis assessing patient survival as a function of the relative indicated mRNA level (high and low) in AC and SCC was performed. The results show that in AC patients, high levels of VDAC1, SMAC, HYOU1, TTLL12, and RAB34 are associated with low survival rates, while high levels of AKR1B10, AIF (mitochondrial), ARL1, TSG101, HAT1, p40, NAPSA, LRRFIP2, TITF1, and WDR82 are associated with higher survival rates (Table 9). In contrast, the expression level of these proteins had no effect on SCC survival rates (Table 9). The data presented in Table 9 were obtained from KMplot-.com. Total sample number was 2437, with initial number in each group presented in parenthesis. The Kaplan-Meier estimator used an earlier (2015) release of the database (Szasz A M, et al. Oncotarget. 2016; 7: 49322-33).

TABLE 9

The relationship between protein expression levels and survival in AC and SCC lung cancer subtypes

| | | Median Survival time (months) | | | | | |
|---|---|---|---|---|---|---|---|
| | | AC | | SCC | | P value | |
| No | Gene symbol | High (No.) | low | high | low | AC | SCC |
| Higher survival associated with low mRNA level | | | | | | | |
| 1. | VDAC1 | 75 (360) | 150 (360) | 40 (262) | 50 (262) | 0.0018 | 0.87 |
| 2. | SMAC | 65 (360) | 120 (360) | 60 (262) | 60 (262) | $7.4 \times 10^{-6}$ | 0.9 |
| 3. | HYOU1 | 65 (360) | 115 (360) | 60 (262) | 60 (262) | $2.2 \times 10^{-6}$ | 0.76 |
| 4. | TILL12 | 75 (337) | 120 (336) | 50 (135) | 55 (136) | $2.9 \times 10^{-4}$ | 0.63 |
| 5. | RAB34 | 90 (337) | 122 (336) | 65 (135) | 45 (136) | 0.013 | 0.087 |
| 6. | MAVS | 90 (337) | 115 (336) | 65 (135) | 50 (136) | 0.13 | 0.25 |
| Higher survival associated with high mRNA level | | | | | | | |
| 7. | ARL1 | 175 (360) | 60 (360) | 50 (261) | 60 (263) | $3.4 \times 10^{-14}$ | 0.84 |
| 8. | TSG101 | 137.5 (360) | 65 (360) | 50 (262) | 50 (262) | $1.9 \times 10^{-9}$ | 0.18 |
| 9. | HAT1 | 118 (360) | 70 (360) | 51 (262) | 60 (262) | 0.0046 | 0.32 |
| 10. | p40 | 115 (360) | 70 (360) | 60 (262) | 60 (262) | $1.4 \times 10^{-7}$ | 0.84 |
| 11. | NAPSA | 130 (337) | 80 (336) | 65 (135) | 50 (136) | $4.2 \times 10^{-5}$ | 0.2 |
| 12. | LRRFIP2 | 120 (361) | 75 (359) | 52 (261) | 52 (263) | 0.02 | 0.51 |
| 13. | AIF (Mitochondrial) | 130 (360) | 90 (360) | 60 (262) | 55 (262) | 0.033 | 0.9 |
| 14. | TITF1 | 127 (360) | 81.3 (360) | 50 (262) | 50 (262) | 0.00051 | 0.11 |
| 15. | WDR82 | 120 (360) | 90 (360) | 50 (262) | 50 (262) | $2 \times 10^{-4}$ | 0.95 |

Example 5: SMAC/Diablo Presence in the Nucleus

Figure 6A:
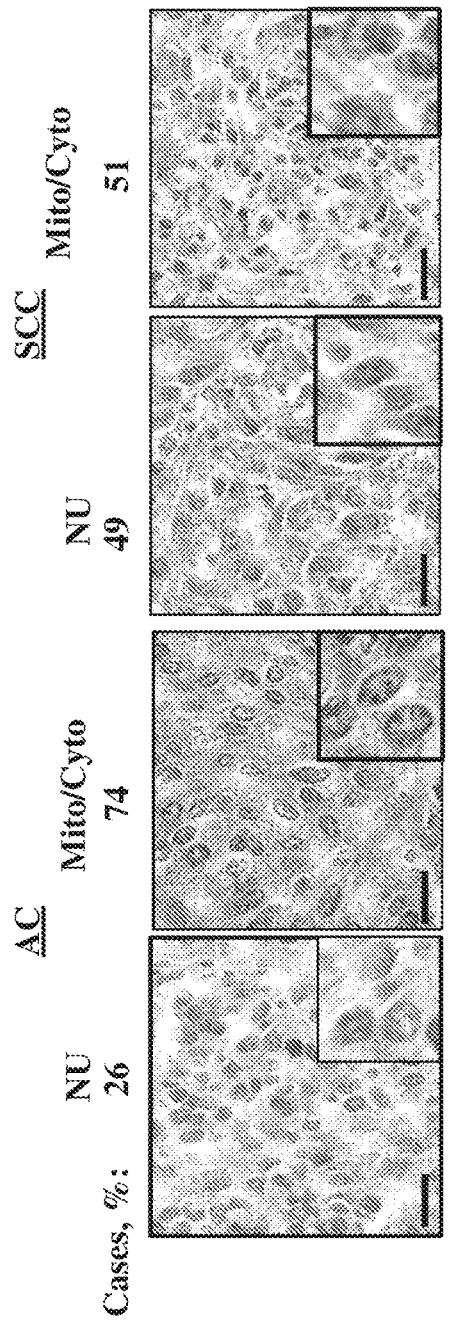
FIG. 6 shows SMAC sub-cellular localization in lung cancer. IHC staining of SMAC (FIG. 6A) and AIF (FIG. 6B) in human SCC and AC lung cancer in tissue array slides (Biomax) with nuclear and cytosolic localization of SMAC shown.
FIG. 6C: nuclear extracts were prepared from AC and SCC samples of lung cancer patient using a nuclear/cytosol fractionation kit (Biovision, Milpitas, Calif.) following the manufacturer's instructions. Following centrifugation (16,000 g, 10 min), the supernatant (cytosolic fraction), and pellet (nuclear fraction) were re-suspended in the original volume and subjected to immunoblotting for SMAC, VDAC1 and AIF.
FIG. 6D: Quantitative analysis, presenting the results as mean±SEM (n=3).
Figure 6B:
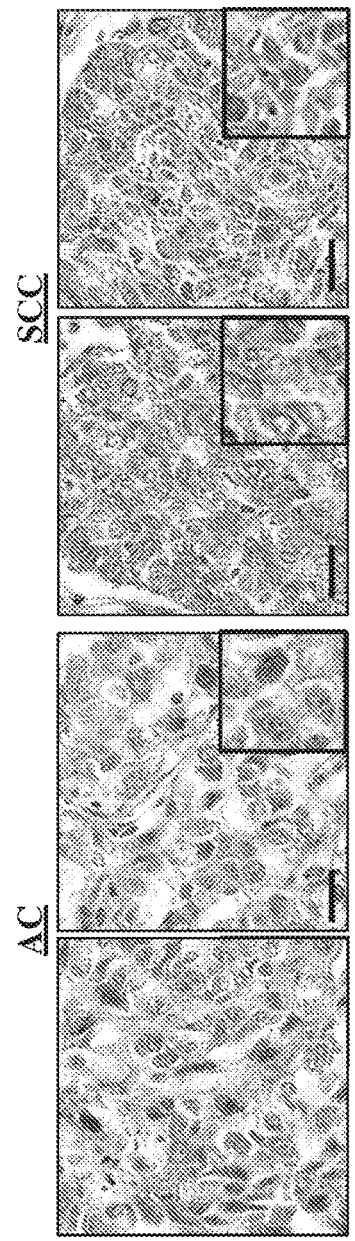

Interestingly, analysis of SMAC/Diablo expression in a tissue array of lung cancer-derived samples revealed that although SMAC is a mitochondrial protein, high levels of the protein were found in the nucleus and cytosol of SCC but only to a lesser extent in AC tissue samples (FIG. 6A). No previous study has reported the presence of SMAC in the nucleus. The results further show that AIF, known to translocate to the nucleus upon apoptosis induction is not present in the nucleus (FIG. 6B).

Figure 6C:
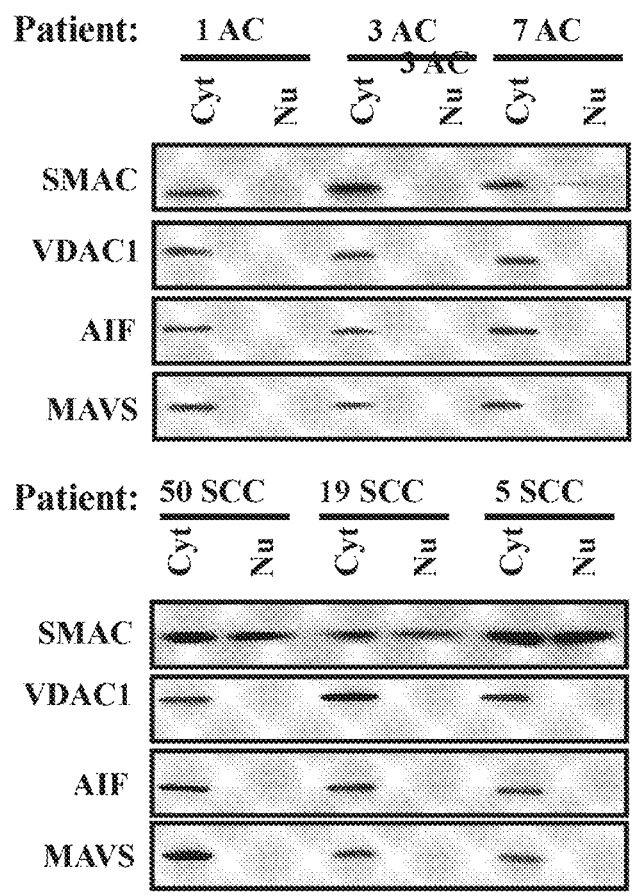
Figure 6D:
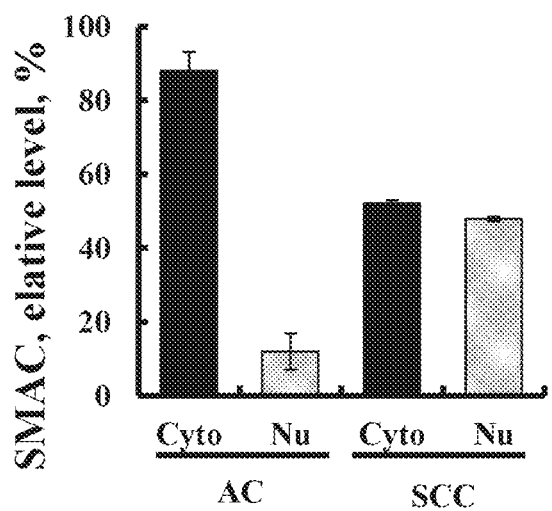

To further demonstrate the presence of SMAC in the nucleus, the nuclear distribution of SMAC in AC and SCC lung cancer samples obtained from healthy and tumor tissues of the same lung was analyzed, after separating the nuclear and the cytosolic fractions (FIG. 6C, D). While in AC about 90% of SMAC was mitochondrial/cytosolic, in SCC about 50% was mitochondrial/cytosolic and 50% was found in the nuclear fraction (FIG. 6D). In the nuclear fraction containing SMAC, three other mitochondrial proteins, VDAC1, MAVS and AIF, were not found (FIG. 6C), indicating the specific nuclear localization of SMAC.

In summary, several biomarkers potentially enable for distinguishing between AC and SCC that are derived from published data, as confirmed here, and have been identified here for the first time were selected based on being differentially expressed in SCC or AC (Table 10).

TABLE 10

Selected biomarkers for distinguishing between AC and SCC
Proteins that can be used as biomarkers are presented, with their expression levels in SCC, relative to AC, as determined by proteomics, qPCR (in parenthesis) and RNASeq studies, listed. The source of the data is also indicated.

| Protein | SCC/AC | | |
|---|---|---|---|
| Method: | Proteomics (qPCR) | RNA Seq | Marker for: |
| HAT1 - Histone acetyltransferase type B | 475 (1.8) | 1.4 | SCC, this study |
| AKR1B10 - Aldo-keto reductase family 1 member B10 (secreted) | 17.9 (20) | 4 | SCC, this study |
| USP14 - Ubiquitin carboxyl-terminal hydrolase 14 | 4.4 (2) | 1.3 | SCC, this study |
| TTLL12 - Tubulin-tyrosine ligase-like protein 12 | 8.1 (5) | 2.5 | SCC, this study |
| LRRFIP - Leucine-rich repeat flightless-interacting protein 2 | 19.3 (3) | 1.1 | SCC, this study |
| WDR82 - WD repeat-containing protein 82 | 9.8 (4.4) | 1 | SCC, this study |

TABLE 10-continued

Selected biomarkers for distinguishing between AC and SCC
Proteins that can be used as biomarkers are presented, with their expression levels
in SCC, relative to AC, as determined by proteomics, qPCR (in parenthesis)
and RNASeq studies, listed. The source of the data is also indicated.

| Protein | SCC/AC | | |
|---|---|---|---|
| Method: | Proteomics (qPCR) | RNA Seq | Marker for: |
| IGF2BP3 - Insulin-like growth factor 2 mRNA-binding protein | 4.9 | 1.8 | SCC, this study |
| ITGA7 - Integrin alpha-7 (Q13683) | 107 | −1.4 | SCC, this study |
| PFN2 - Profilin-2 | 4.9 | 2.7 | SCC, this study |
| TSG101 - Tumor susceptibility gene 101 protein | −38.3 (−1.6) | −1.1 | AC, this study |
| ACOT1 - Acyl-coenzyme A thioesterase 1 | −2.8 | −1.7 | AC, this study |
| RAB34 - Ras-related protein Rab-34 | −6.0 | −1.3 | AC, this study |
| ACAD8 - Isobutyryl-CoA dehydrogenase, mitochondrial | −17 | −2.4 | AC, this study |
| SMAC - Second mitochondria-derived activator of caspases | Nuclear localization in SCC | | SCC, this study |
| Ck5 - Keratin, type II cytoskeletal 5 | 4.6 | 67.5 | SCC |
| Ck13 - Keratin, type I cytoskeletal 13 | 4.4 | 63.7 | SCC |
| Ck14 - Keratin, type I cytoskeletal 14 | 3.2 | 59.2 | SCC |
| Ck17 - Keratin, type I cytoskeletal 17 | 2.1 | 19.5 | SCC |
| GGH Gamma-glutamyl hydrolase (secreted) | | 1.9 | SCC |
| NAPSA - Napsin A aspartic peptidase | — | −10 | AC |
| FEN1 - Flap endonuclease 1 | 3.5 | 1.5 | AC |
| AZGP1 - Zinc-alpha-2-glycoprotein (secreted) | −2.7 | −4.1 | AC |
| NPC2 Epididymal secretory protein E1 (secreted) | | −2.1 | AC |

Example 6: Silencing of APOOL, VPS29, and CAF17 for Treating NSCLC

To verify the importance of the proteins identified to be overexpressed in NSCLC, the effects of their silencing by specific siRNA is examined. At least one siRNA, and typically two siRNAs are designed for silencing the RNA encoding each of the proteins APOOL, VPS29, and CAF17. In addition, a non-specific scarmbeled siRNA is designed.

In Vitro Assay

Cells of NSCLC cell line are transected with scrambled siRNA or with the siRNA specific to each protein and cell growth is analyzed using the Sulforhodamine B (SRB) method. In this method, forty-eight or 96 h post-transfection with siRNA, cells are washed twice with PBS, fixed with 10% trichloroacetic acid for 1-2 h, and subsequently stained with SRB. SRB is extracted from the cells using 100 mM Tris-base and absorbance at 510 nm is determined using an Infinite M1000 plate reader (Tecan, Mannedorf, Switzerland).

In Vivo Assay-Xenograft Experiments Using Nude Mice.

A549 lung cancer cells ($7 \times 10^7$) are injected s.c. into the hind leg flanks of Athymic 8-weekold male SCID nude mice. Eleven days after inoculation, the developing tumors are measured in two dimensions with a digital caliper and tumor volume is calculated as follows: volume=$X2 \times Y/2$, where X and Y are the short and long tumor dimensions, respectively. The mice with xenografts reaching a volume of 65-100 mm$^3$ are randomized for different treatments (eight or nine animals in each group): PBS, non-targeting (scrambled) siRNA or siRNA against the selected protein. Each treatment substance is injected into the established s.c. tumors using the jetPEI delivery reagent (10 µg siRNA/20-µl jetPEI). The xenografts are injected (20 µl per tumor) with PBS or the appropriate siRNA every 3 days. Beginning on the day of inoculation, mouse weight and tumor volume are monitored twice a week for a period of 33 days using a digital caliper. At the end point of the experiment, i.e., when tumor volume reached ~250 mm$^3$, the mice are sacrificed using $CO_2$ gas; the tumors are excised and ex vivo weight is determined. Half of each tumor is fixed in 4% buffered formaldehyde, paraffin-embedded and processed for histological examination, while the second half is frozen in liquid nitrogen and stored in −80° C. for immunoblot analysis.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a subject diagnosed to have non-small cell lung carcinoma (NSCLC) subtype SCC comprising the steps of:
   a. diagnosing the NSCLC subtype, comprising
      i. determining the expression level of a biomarker selected from a protein and mRNA encoding said protein in a biological sample obtained from the subject, wherein the biomarker is ITGA7;
      ii. comparing the expression level of said biomarker to the expression level of said biomarker in a healthy biological sample and/or a reference value representing healthy biological sample;
      iii. computing a fold change of the expression level of said biomarker in the sample obtained from said subject and the expression level in the healthy sample and/or reference value;
      iv. diagnosing said subject as having NSCLC subtype SCC, wherein an equal or elevated fold change of the biomarker ITGA7 compared to a reference value indicates that the subject has NSCLC subtype SCC, wherein the reference value is derived from the fold change of the expression of said ITGA7 biomarker in a plurality of samples obtained from SCC patients compared to its expression in a plurality of healthy biological samples; and
   b. treating the subject diagnosed to have NSCLC subtype SCC with a therapy comprising administering to the subject a therapeutically effective amount of at least one agent that reduces the expression or activity of at least one protein selected from the group consisting of HAT1, LRRFIP2, AKR1B10, WDR82, TTL12, IGF2BP3, and ITGA7.

2. The method of claim 1, wherein the biomarker is a protein.

3. The method of claim 1, wherein the biological sample obtained from the subject diagnosed to have NSCLC is a lung tissue sample, and wherein the healthy biological sample is selected from the group consisting of a sample obtained from a healthy subject and a sample obtained from a healthy lung tissue of the subject suspected to have NSCLC.

4. The method of claim 1, wherein the biological sample obtained from the subject diagnosed to have NSCLC is selected from the group consisting of blood, blood plasma and serum sample.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
actcttccag ccttccttcc                      20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgttggcgta caggtctttg                      20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gagcaggacg tgagacttct                      20

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tttgccaaga ggagacttcc aa                   22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tgcccttaaa aggtatgcag gt                   22

<210> SEQ ID NO 6
<211> LENGTH: 20
<212> TYPE: DNA
<213> ORGANISM: Artificial Sequence
<220> FEATURE:

```
<223> OTHER INFORMATION: Primer

<400> SEQUENCE: 6
tctcggcaaa ctgtgggaaa                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tggagcacga ggttttcgac                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cgatgacctt gtagcacagc                                               20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gccagctcaa gaaaatggtg t                                             21

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
aggtctctgt atttgtactg ggt                                           23

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cctcagcaac aacccctcta                                               20

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggtcatagat atcccgcaat tca                                           23
```

```
<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcttcgattt cagccccaac                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tctctttggt ttgccctcct                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
atggcgggat ttggtgctat                                               20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gttcaattgc tgtgttggtg t                                             21
```